(12) United States Patent
Matsumura et al.

(10) Patent No.: US 7,433,731 B2
(45) Date of Patent: Oct. 7, 2008

(54) BIOLOGICAL SIGNAL DETECTION SYSTEM

(75) Inventors: Fumiyuki Matsumura, Tokyo (JP); Tetsushi Sekiguchi, Tokyo (JP); Hiroshi Sakata, Tokyo (JP); Hidehiro Hosaka, Saitama (JP); Shin Suda, Tokyo (JP); Kohei Ono, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 11/020,221

(22) Filed: Dec. 27, 2004

(65) Prior Publication Data

US 2005/0107714 A1 May 19, 2005

Related U.S. Application Data

(60) Division of application No. 09/659,605, filed on Sep. 11, 2000, now Pat. No. 6,856,832, which is a continuation-in-part of application No. 09/220,751, filed on Dec. 28, 1998, now Pat. No. 6,161,036.

(30) Foreign Application Priority Data

| Dec. 25, 1997 | (JP) | ................................... 9-358536 |
| Dec. 26, 1997 | (JP) | ................................... 9-359933 |
| Sep. 9, 1999 | (JP) | ................................... 11-255483 |
| Sep. 13, 1999 | (JP) | ................................... 11-258906 |

(51) Int. Cl.
*A61B 5/0408* (2006.01)

(52) U.S. Cl. .................................................... 600/509

(58) Field of Classification Search ................. 600/382, 600/386, 388–391, 393, 520, 509
See application file for complete search history.

(56) References Cited

U.S. PATENT DOCUMENTS

| 4,318,412 | A | * | 3/1982 | Stanly et al. ................. 600/508 |
| 5,042,481 | A | * | 8/1991 | Suzuki et al. ................ 600/393 |
| 5,092,340 | A | * | 3/1992 | Yamaguchi et al. ......... 600/508 |
| 5,181,025 | A | | 1/1993 | Ferguson et al. |
| 5,348,008 | A | * | 9/1994 | Bornn et al. ................. 600/301 |

(Continued)

FOREIGN PATENT DOCUMENTS

| GB | 2261290 A | 5/1993 |
| JP | 4-117606 | 10/1992 |
| JP | 9-224917 | 9/1997 |
| JP | 10-234688 | 9/1998 |
| JP | 11-70086 | 3/1999 |
| JP | 11-259783 | 9/1999 |
| WO | WO 94/01039 A1 | 1/1994 |

OTHER PUBLICATIONS

European Search Report for Appln. No. EP 98 12 4770, dated Jan. 5, 2001, Nihon Kohden Corporation.

*Primary Examiner*—George R Evanisko
(74) *Attorney, Agent, or Firm*—Sughrue Mion, PLLC

(57) ABSTRACT

A biological signal detection system includes a pair of electrodes, adapted to be attached on a living body; a transmitter, adapted to be attached on the living body, and including an electric circuit operable to process the biological signal and to telemeter the processed signal; and a biological signal inputting apparatus. The system may also include a receiver-transmitter operable to receive the processed signal telemetered from the transmitter and to telemeter the processed signal to the biological signal inputting apparatus by way of a wide area network; and a storage for storing the processed signal telemetered from the transmitter as biological signal data and for inputting the biological signal data to the biological signal inputting apparatus. Also, the system may include a storage for storing the processed signal telemetered from the transmitter as biological signal data and for inputting the biological signal data to the biological signal inputting apparatus.

7 Claims, 17 Drawing Sheets

U.S. PATENT DOCUMENTS

| | | | |
|---|---|---|---|
| 5,353,793 A * | 10/1994 | Bornn | 600/386 |
| 5,445,149 A * | 8/1995 | Rotolo et al. | 600/382 |
| 5,458,124 A * | 10/1995 | Stanko et al. | 600/509 |
| 5,511,553 A * | 4/1996 | Segalowitz | 600/508 |
| 5,673,054 A | 9/1997 | Hama | |
| 5,752,976 A | 5/1998 | Duffin et al. | |
| 5,862,803 A * | 1/1999 | Besson et al. | 600/508 |
| 5,947,897 A | 9/1999 | Otake | |
| 6,117,077 A * | 9/2000 | Del Mar et al. | 600/301 |
| 6,238,338 B1 * | 5/2001 | DeLuca et al. | 600/300 |
| 6,259,939 B1 | 7/2001 | Rogel | |
| 6,654,626 B2 * | 11/2003 | Devlin et al. | 600/383 |

* cited by examiner

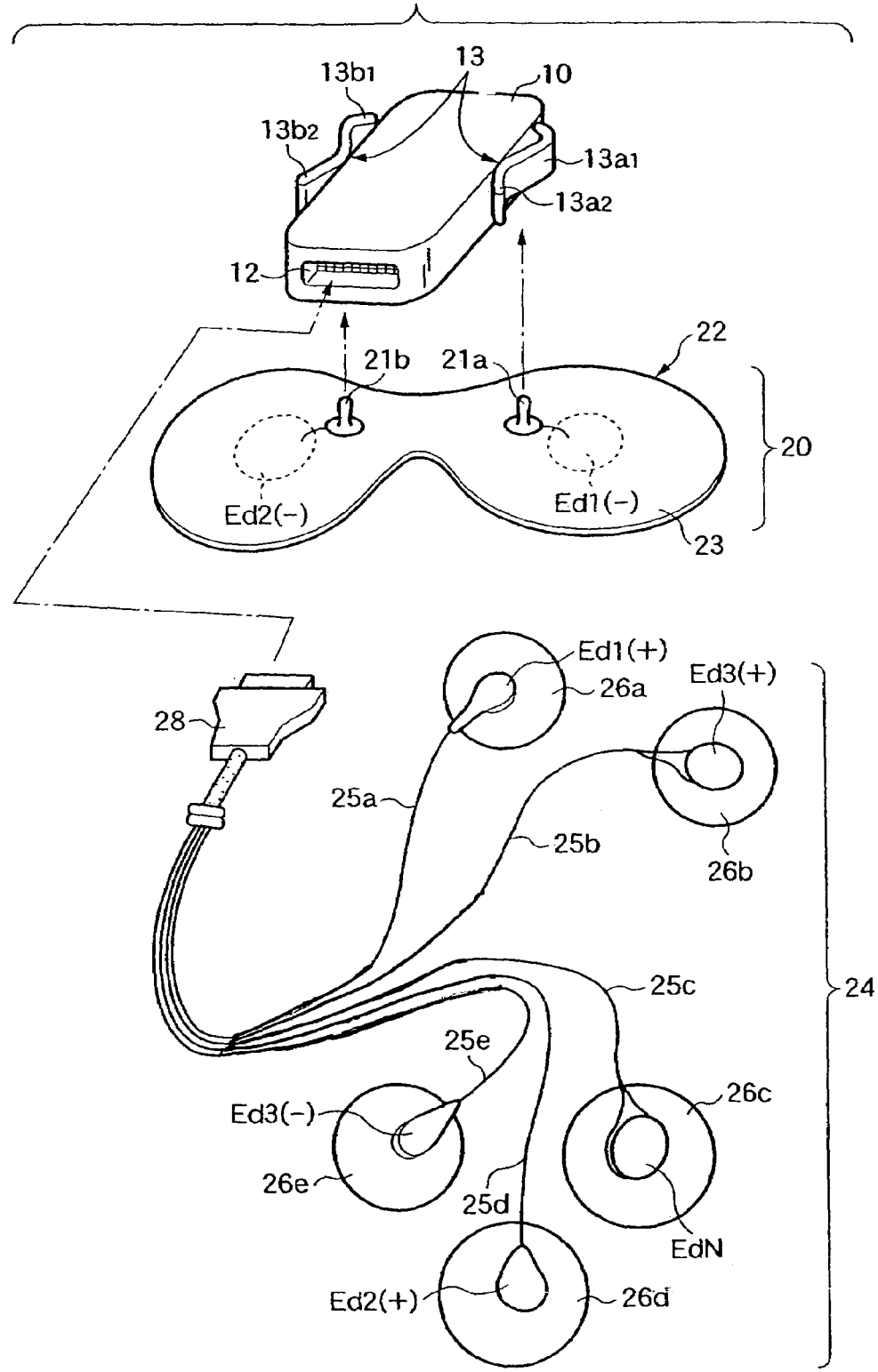

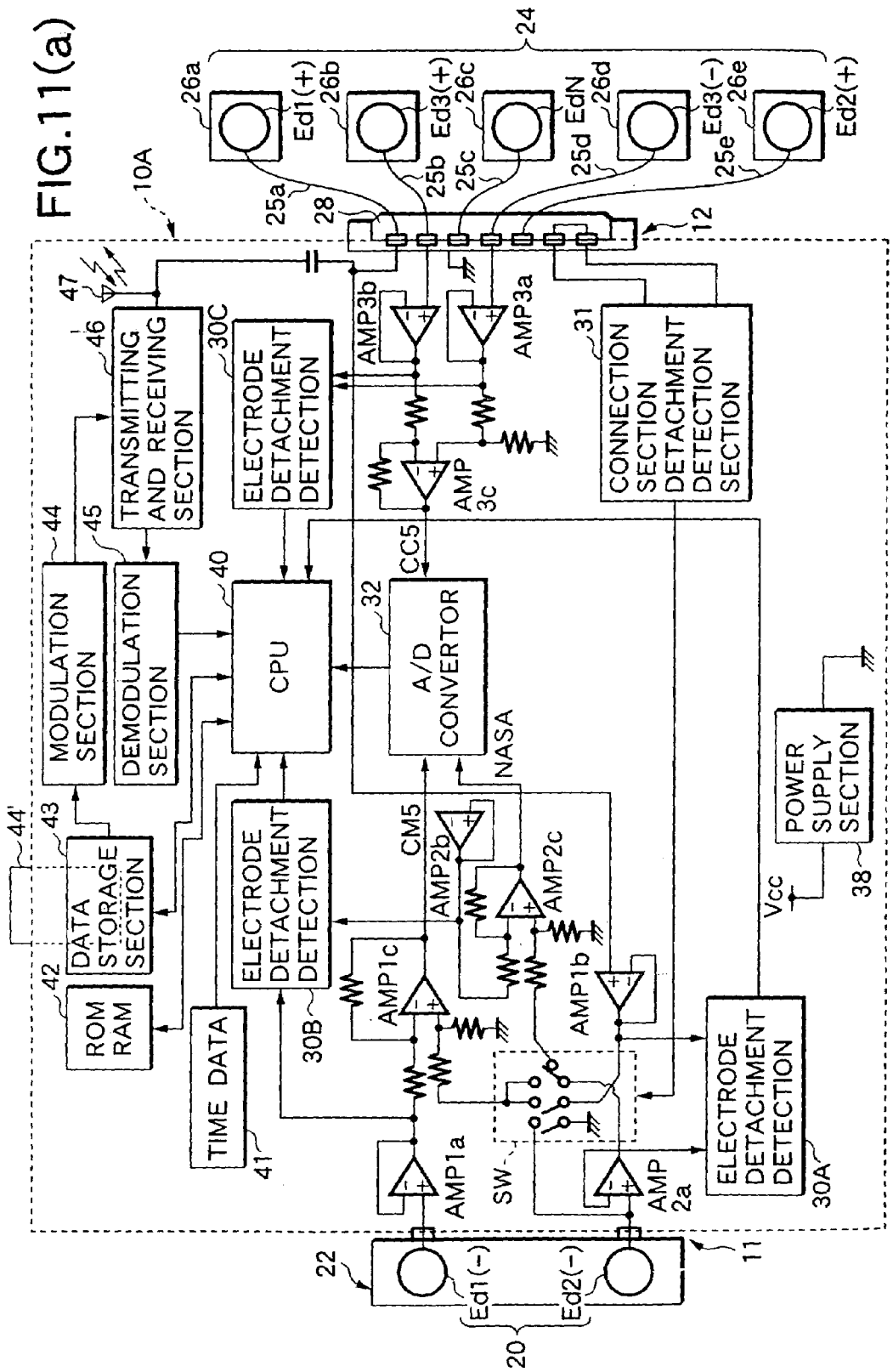

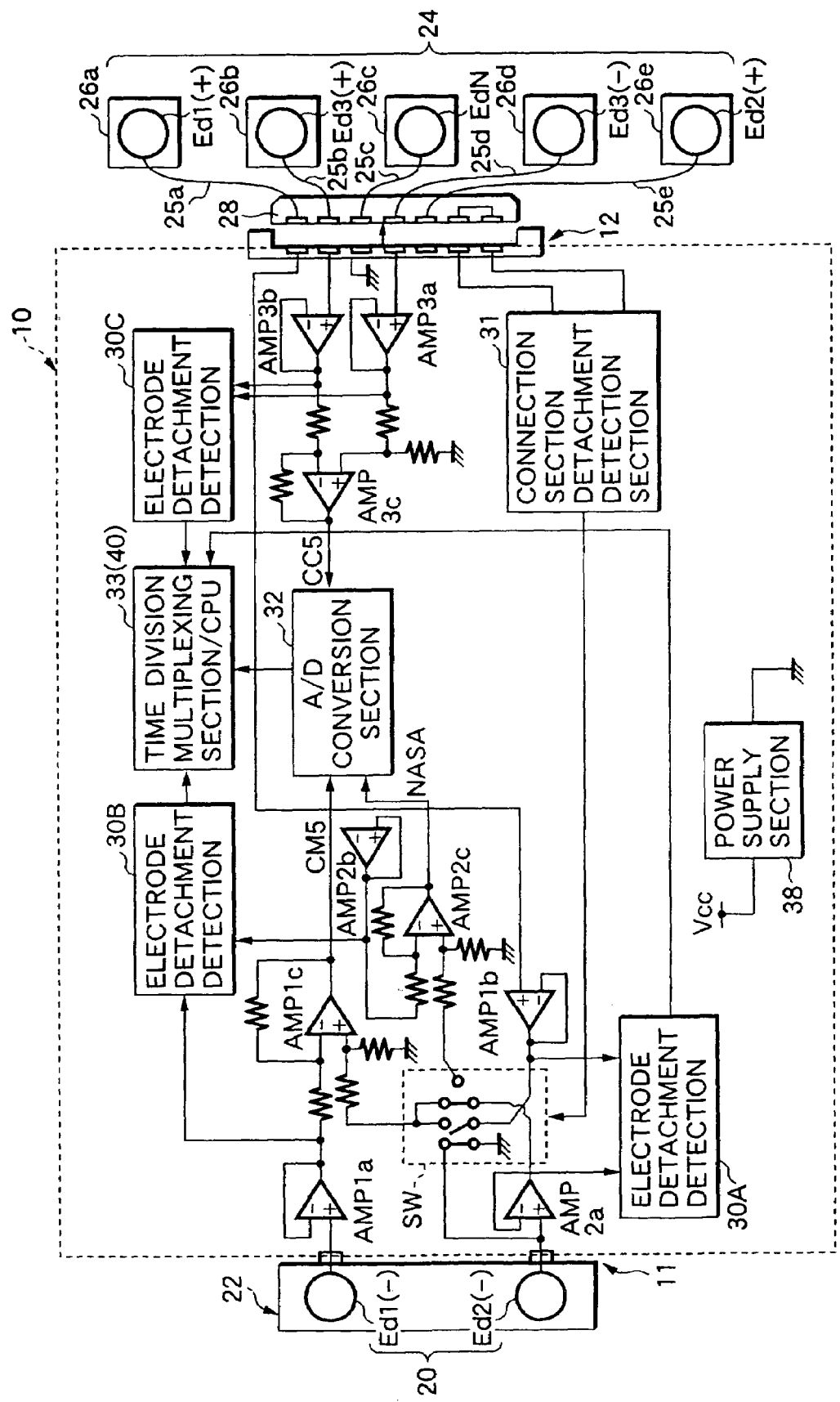

BIOLOGICAL SIGNAL DETECTION SYSTEM

This is a divisional application of U.S. patent application Ser. No. 09/659,605, filed Sep. 11, 2000 (now U.S. Pat. No. 6,856,832), which is a continuation-in-part application of U.S. patent application Ser. No. 09/220,751, filed Dec. 28, 1998 (now U.S. Pat. No. 6,161,036).

BACKGROUND OF INVENTION

1. Field of invention

This invention relates to a biological signal detection apparatus and in particular to a biological signal detection apparatus applicable to a medical telemetry system wherein a biological signal detected by an electrode attached to the living tissue surface of a patient can be appropriately processed and the provided signal can be telemetered by a transmitter and can be received at a remotely located monitor for monitoring the disease condition of the patient, and a Holter electrocardiograph incorporating the biological signal detection apparatus.

Further, this invention relates to a communication system of detection data, etc., provided by detecting biological signals and in particular to a communication system for transmitting and receiving biological signals detected by a Holter electrocardiograph.

2. Related art

To care for a seriously ill patient directly linked to his or her life as in an ICU (intensive care unit) or a CCU (coronary care unit), biological information needs to be continuously monitored to precisely keep track of the conditions of the patient. Thus, it is important to provide information necessary for treatment conducted at the bedside of the patient using a bedside monitor placed at the bedside of the patient. It is also important to find out an anomaly of the patient promptly and issue an alarm and send data provided from the biological information of the patient to a central monitor placed in a nurse station, a doctor room, etc.

From the viewpoint, hitherto, to collect necessary data and display the data on monitors placed on the periphery to provide biological information of a patient in moving the patient in emergency, at the bedside of the patient in a hospital, etc., a medical telemetry system of transmitting and receiving wireless signals has been used simply and efficiently to input signals detected by a biological signal detection apparatus made up of various sensor electrodes, etc., attached to the living tissue surfaces of the patient.

Hitherto, as a biological signal measuring apparatus of converting a biological signal of a patient, etc., into telemetry (cordless) and measuring, a biological signal measuring apparatus has been proposed (Japanese Utility Model Registration No. 2558836), the biological signal measuring apparatus comprising a sensor section made up of three electrode parts for detecting a biological signal, a transmission section for transmitting the biological signal detected by each electrode part of the sensor section to an external reception section, and a power supply section for supplying power to the transmission section, wherein the transmission section has the power supply section integrally and can be directly attached and detached by being fitted to any one of the three electrode parts, wherein three contacts corresponding to signal lines from the three electrode parts form contacts made flush with each other, wherein the biological signals detected by the three electrode parts are input to the transmission section, and wherein the electrode parts are made disposable and the transmission section can be recycled.

That is, in the biological signal measuring apparatus according to the proposition, the transmission section containing the power supply section is made integral with anyone of the three electrode parts and the biological signals detected by the electrode parts are input to the transmission section, whereby the constraint feeling of the patient is improved remarkably and no signal cable exists between the transmission section and the sensor section, thus extra connection points are excluded and therefore stable measuring can be conducted over a long time and the reliability is enhanced.

A Holter electrocardiograph apparatus that can improve the convenience of a communication interface with a computer for analyzing, storing, and arranging data by providing an already existing portable Holter electrocardiograph apparatus with an infrared communication apparatus for inputting electrocardiogram data to a computer in noncontact for storing and analyzing the data simply or by transmitting electrocardiogram data sampled from a patient and compressed to a remotely located computer for storing and analyzing the data using a public telemetry network applied to portable telephones, portable information terminals, etc., has been proposed (JP-A-9-224917).

That is, this Holter electrocardiograph apparatus according to the proposition is characterized by the fact that an already existing portable Holter electrocardiograph apparatus comprises an infrared communication apparatus as means for inputting highly compressed data stored in memory to an external machine, and the infrared communication apparatus comprises means for communicating according to a predetermined procedure for a computer and inputting monitored electrocardiogram data to the computer in noncontact at high speed. Further, the Holter electrocardiograph apparatus can be configured to use a public telemetry network applied to portable telephones and portable information terminals to transmit highly compressed electrocardiogram data to a remotely located computer for storing and analyzing the data.

A portable electrocardiogram monitor for monitoring a plurality of electrocardiogram signals led by the electrode attached to the chest of a patient by a monitor circuit carried by the patient and telemetering arrhythmia information detected in the electrocardiogram signals to an emergency medical institution for receiving rescue of diagnosis, instruction for the patient, first aid to be given to the patient, etc., by the expert (JP-A-10-234688).

That is, the portable electrocardiogram monitor according to the proposition comprises chest side circuitry attached to the chest of a patient and waist side circuitry attached to the waist of the patient. The chest side circuitry has addition means for adding electrocardiogram signals of a plurality of channels and intra-monitor transmission means for telemetering the added electrocardiogram signal provided by the addition means from the chest to the waist and the waist side circuitry has reception means for receiving the transmission signal of the intra-monitor transmission means, arrhythmia detection means for detecting severe arrhythmia that is unignorable in the added electrocardiogram signal received by the reception means, and external transmission means for telemetering information indicating occurrence of arrhythmia together with the identification signal of the patient to an emergency medical institution.

However, in the biological signal measuring apparatus according to the proposition, if the transmission section having the three electrode parts inputs the biological signal detected by each electrode part and transmits the signal to the outside and is applied as a Holter electrocardiograph, the method of the electrode positioning for providing electrocardiogram data, namely, the position leading electrode-to-electrode potential does not match the position of the electrode that can be led properly and efficiently as a Holter electrocardiograph, thus simple and prompt electrocardiogram data cannot be provided.

In the Holter electrocardiograph apparatus according to the proposition, an already existing portable Holter electrocardiograph apparatus is provided with an infrared communication apparatus, whereby electrocardiogram data is transmitted to a personal computer or a remotely located computer in non-contact for smoothly storing and analyzing the data and the existing portable Holter electrocardiograph apparatus itself is not improved or modified. Thus, for example, improvement or prevention means for occurrence of inconvenience or discomfort when the electrodes are attached to the patient or occurrence of a malfunction caused by detachment of the electrode is not considered at all. Further, the Holter electrocardiograph apparatus assumes only that the patient sends electrocardiogram data to a medical institution, and the patient must perform the operation of transmitting electrocardiogram data consciously; the operation is burdensome for the patient.

In the portable electrocardiogram monitor according to the proposition, the arrhythmia detection means is attached to the patient, severe arrhythmia that is unignorable is determined by hardware or software analysis means, and electrocardiogram information at the time is sent. Thus, the information is insufficient for the doctor to finally diagnose the conditions of the patient. If determination of the arrhythmia detection means attached to the patient is only made, when erroneous detection occurs, it is feared that a serial problem that may be developed to a lawsuit against the doctor (for example, electrocardiogram information is not transmitted although the patient is in an actually critical condition) may occur.

Further, in the apparatus according to the propositions, the fact that it is made possible to telemeter biological signals of a patient to a remotely located monitor is disclosed or suggested, but the configuration of a medical telemetry system for making it possible to smoothly and simply exchange information between the patient and the monitor is not specifically proposed at all.

SUMMARY OF INVENTION

As a result of repeating research and trials assiduously, the inventor et al have found out that a communication system of detection data, etc., provided by detecting a biological signal, which can construct a medical telemetry system that can prevent detachment of an electrode from causing a malfunction to occur and can smoothly and simply exchange information between a patient and a monitor can be provided, the communication system adopting the configuration comprising a Holter electrocardiograph comprising a biological signal detection apparatus comprising a plurality of electrodes for detecting a biological signal, supports being attached to the living tissue surface of a patient for supporting the electrodes, and a transmitter for processing the signal detected by the electrode and telemetering the detected signal, a receiver for receiving the signal telemetered from the transmitter of the biological signal detection apparatus and demodulating the received signal, the receiver comprising a terminal for outputting the demodulated signal to a biological signal input section of required record means, and a recorder comprising record means for recording the demodulated signal output from the terminal of the receiver, wherein the recorder of the Holter electrocardiograph comprises transmitting and receiving means for telemetering the signal stored in the record means, receiving an external transmission signal, and telemetering some or all of the signals stored in the record means as instructed by the external transmission signal, and a biological signal input apparatus comprising transmitting and receiving means for inputting signals and transmitting and receiving communication information to and from the transmitting and receiving means of the recorder of the Holter electrocardiograph through a relay transmitter-receiver and a wide area network is provided.

It is therefore an object of the invention to provide a biological signal detection apparatus that can construct a medical telemetry system that can eliminate inconvenience or discomfort when the electrodes are attached to a patient and can prevent detachment of an electrode from causing a malfunction to occur and smoothly and simply exchange information between a patient and a monitor.

It is another object of the invention to provide an easy-to-handle Holter electrocardiograph which enables the user to properly and promptly monitor electrocardiogram data of a patient by applying such a biological signal detection apparatus.

It is therefore another object of the invention to provide a communication system of biological signals that can construct a medical telemetry system that can prevent detachment of an electrode from causing a malfunction to occur and can smoothly and simply exchange information between a patient and a monitor.

To the end, according to the invention, there is provided a biological signal detection apparatus comprising a first electrode group for detecting a biological signal, a first support being attached to the living tissue surface of a patient for supporting the first electrode group, a second electrode group for detecting a biological signal, a second support being attached to the living tissue surface for supporting the second electrode group, and a transmitter comprising an electric circuit for processing the signals detected by the first and second electrode groups and telemetering the detected signals, characterized in that the transmitter comprises a first connection section for electrically connecting the first electrode group to the transmitter and fixing the transmitter directly onto the first support and a second connection section for electrically connecting signal lines from the second electrode group to the transmitter.

In this case, a biological signal potential difference between at least one electrode in the first electrode group and at least one electrode in the second electrode group can be measured (CM5 lead and/or NASA lead).

A potential difference between at least one pair of electrodes in the second electrode group can be measured (CC5 lead).

In the biological signal detection apparatus, the electric circuit for telemetering the detected signals comprises:

a connection section detachment detection section for determining whether or not the second electrode group is connected in the second connection section; and a switch section for measuring the biological signal potential difference between at least one pair of electrodes in the first electrode group if the connection section detachment detection section determines that the second electrode group is not connected in the second connection section and measuring the biological signal potential difference between at least one electrode in the first electrode group and at least one electrode in the second electrode group is measured (CM5 lead and/or NASA lead) if the connection section detachment detection section determines that the second electrode group is connected in the second connection section.

As an alternative, according to the invention, there is provided a biological signal detection apparatus comprising a first electrode group for detecting a biological signal, a first support being attached to the living tissue surface of a patient for supporting the first electrode group, a second electrode group for detecting a biological signal, a second support being attached to the living tissue surface for supporting the second electrode group, and an electric circuit for processing the signals detected by the first and second electrode groups, wherein the electric circuit can comprise a first connection section for electrically connecting the first electrode group to the electric circuit and fixing the electric circuit directly onto the first support and a second connection section for electrically connecting signal lines from the second electrode group to the electric circuit, and wherein detachable storage means being contained in a housing for storing the signals processed by the electric circuit can be provided.

According to the invention, there is provided a biological signal detection apparatus comprising a first electrode group for detecting a biological signal, a first support being attached to the living tissue surface of a patient for supporting the first electrode group, a second electrode group for detecting a biological signal, a second support being attached to the living tissue surface for supporting the second electrode group, an electric circuit for processing the signals detected by the first and second electrode groups, storage means for storing the signals processed by the electric circuit, and a transmitter-receiver for telemetering the signals processed by the electric circuit and the signals stored in the storage means and receiving an external transmission signal, wherein the transmitter-receiver can telemeter some or all of the signals stored in the storage means or the signal processed by the electric circuit as instructed by the external transmission signal.

A Holter electrocardiograph provided by applying a biological signal detection apparatus according to the invention comprises:

a biological signal detection apparatus comprising a first electrode group for detecting a biological signal, a first support being attached to the living tissue surface of a patient for supporting the first electrode group, a second electrode group for detecting a biological signal, a second support being attached to the living tissue surface for supporting the second electrode group, and a transmitter comprising an electric circuit for processing the signals detected by the first and second electrode groups and telemetering the detected signals, the transmitter comprising a first connection section for electrically connecting the first electrode group to the transmitter and fixing the transmitter directly onto the first support and a second connection section for electrically connecting signal lines from the second electrode group to the transmitter;

a receiver for receiving the signal telemetered from the transmitter of the biological signal detection apparatus and demodulating the received signal, the receiver comprising a terminal for outputting the demodulated signal to a biological signal input section of required record mean; and a recorder comprising record means for recording the demodulated signal output from the terminal of the receiver.

To the end, according to the invention, there is provided a communication system of biological signals, comprising a Holter electrocardiograph comprising a biological signal detection apparatus comprising a plurality of electrodes for detecting a biological signal, supports being attached to the living tissue surface of a patient for supporting the electrodes, and a transmitter for processing the signal detected by the electrode and telemetering the detected signal, a receiver for receiving the signal telemetered from the transmitter of the biological signal detection apparatus and demodulating the received signal, the receiver comprising a terminal for outputting the demodulated signal to a biological signal input section of required record means, and a recorder comprising record means for recording the demodulated signal output from the terminal of the receiver, characterized in that the recorder of the Holter electrocardiograph comprises transmitting and receiving means for telemetering the signal stored in the record means, receiving an external transmission signal, and telemetering some or all of the signals stored in the record means as instructed by the external transmission signal, and characterized by a biological signal input apparatus comprising transmitting and receiving means for inputting signals and transmitting and receiving communication information to and from the transmitting and receiving means of the recorder of the Holter electrocardiograph through a relay transmitter-receiver and a wide area network.

As an alternative, according to the invention, there is provided a communication system of biological signals, comprising a Holter electrocardiograph comprising a biological signal detection apparatus comprising a plurality of electrodes for detecting a biological signal, supports being attached to the living tissue surface of a patient for supporting the electrodes, an electric circuit for processing the signal detected by the electrode, storage means for storing the signal processed by the electric circuit, and a transmitter-receiver for telemetering the signal processed by the electric circuit and the signal stored in the storage means and telemetering some or all of the signals stored in the storage means or the signal processed by the electric-circuit as instructed by an external transmission signal, wherein a biological signal input apparatus comprising transmitting and receiving means for inputting signals and transmitting and receiving communication information to and from the transmitter-receiver of the Holter electrocardiograph through a relay transmitter-receiver and a wide area network is provided.

In the communication system, the relay transmitter-receiver can transmit and receive the communication information between the transmitting and receiving means or the transmitter-receiver placed in the recorder of the Holter electrocardiograph and the wide area network, and the wide area network can be adapted to transmit and receive the communication information between the relay transmitter-receiver and the transmitting and receiving means of the biological signal input apparatus.

In the communication system, the biological signal input apparatus can comprise:

input data instruction means for indicating data to be input among the signals stored in the record means placed in the recorder of the Holter electrocardiograph or stored in the storage means placed in the transmitter-receiver;

instruction information transmission means for transmitting instruction information specified by the input data instruction means to the record means placed in the recorder of the Holter electrocardiograph or the storage means placed in the transmitter-receiver via the wide area network and the relay transmitter-receiver;

input reception means for receiving the signal transmitted based on the instruction information from the transmitting and receiving means or the transmitter-receiver placed in the recorder of the Holter electrocardiograph via the relay transmitter-receiver and the wide area network; and input storage means for storing the signal received by the input reception means.

The communication system can further include:

non-reception signal generation means for generating a non-reception signal while a radio signal transmitted from the transmitter or the transmitter-receiver of the biological signal detection apparatus cannot be received in the Holter electrocardiograph; and record means for recording the non-reception signal generated by the non-reception signal generation means.

The communication system can further include:

electrode detachment signal generation means for recognizing detachment of one of the electrodes from the living tissue surface by a radio signal transmitted from the transmitter or the transmitter-receiver of the biological signal detection apparatus in the Holter electrocardiograph and generating an electrode detachment signal while the electrode is detached; and record means for recording the electrode detachment signal generated by the electrode detachment signal generation means.

Further, according to the present invention, there is provided that a biological signal detection system comprising:

electrodes for detecting a biological signal;

supports, attached to the living tissue, for supporting said electrodes;

a transmitter including:

an electric circuit for processing the signals detected by said electrodes;

storage means for storing the signals processed by said electric circuit; and a transmitter-receiver for telemetering the signals processed by said electric circuit and the signals stored in said storage means and receiving an external transmission signal, said transmitter-receiver telemeters some or all of the signals stored in said storage means or the signal processed by said electric circuit as instructed by the external transmission signal.

BRIEF DESCRIPTION OF THE DRAWINGS

In the accompanying drawings:

FIG. 2(b) is a schematic perspective view to show a modified example of the main components of the biological signal detection apparatus shown in FIG. 2(a);

FIG. 11(a) is a schematic block diagram to show a configuration example of a biological signal detection apparatus applied to the communication system according to the invention shown in FIG. 10;

FIG. 15 is a block diagram to describe the operation in a connection section detachment detection state in the communication system of biological signals according to the invention.

DETAILED DESCRIPTION OF EXEMPLARY EMBODIMENTS

Referring now to the accompanying drawings, there are shown preferred embodiments of communication system of biological signals according to the invention.

Figure 1:
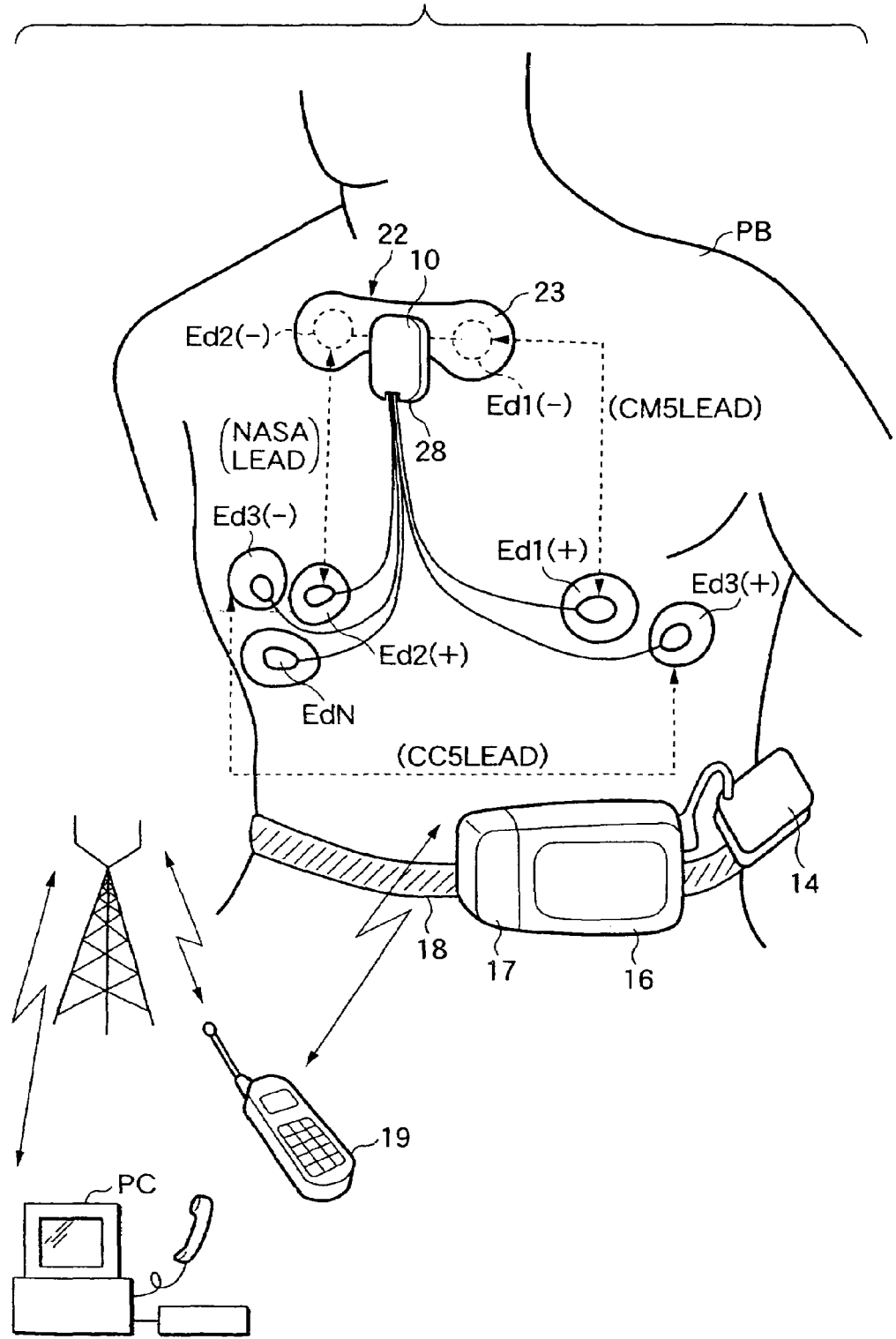
FIG. 1 is a schematic representation to show one embodiment of a basic system configuration of a communication system of biological signals according to the invention.

Basic system configuration for communicating detected data provided by detecting biological signal FIG. 1 is a schematic representation to show a Holter electrocardiograph attached to the body surface of a patient PB for recording electrocardiogram data and a schematic configuration of a communication system for inputting the electrocardiogram data to a remotely located central monitor, etc. In FIG. 1, the Holter electrocardiograph comprises a transmitter 10 attached to the body surface of the patient PB for detecting and telemetering a biological signal (electrocardiogram signal), a receiver 14 for receiving and demodulating the signal telemetered from the transmitter 10, and a recorder 16 made up of various record means for recording the signal (electrocardiogram signal) received and demodulated by the receiver 14. The receiver 14 and the recorder 16 are connected by wire and are attached to parts of the body of the patient PB via a belt 18, etc.

As the communication system with the Holter electrocardiograph, the recorder 16 is provided with transmitting and receiving means 17 for transmitting and receiving signals to and from the outside and the transmitting and receiving means 17 is connected to a biological signal input apparatus implemented as a personal computer PC, etc., via relay transmitting and receiving means 19 such as a portable telephone using a wide area network.

The transmitter 10 will be discussed also with reference to FIG. 2(a). A first electrode group 20 for detecting a biological signal of the patient PB and a first support 22 attached to the living tissue surface of the patient for supporting the first electrode group 20 can be joined detachably and a second electrode group 24 for detecting a biological signal of the patient PB and second supports 26a to 26e attached to the living tissue surface of the patient PB for supporting the second electrode group 24 can be joined detachably.

That is, as joining of the transmitter 10 and the first support 22 and the second supports 26a to 26e, the first support 22 comprises on the inner side, electrodes Ed1 (−) and Ed2 (−) for positioning at symmetrical positions on the upper end of the sternum of the patient PB as an adhesive pad 23 directly attached to the living tissue surface, namely, the body surface (skin). Connection terminals 21a and 21b electrically connected to the electrodes Ed1 (−) and Ed2 (−) are placed on the outer side of the first support 22 implemented as the adhesive pad 23. The transmitter 10 is provided with first connection sections 11 that can be joined to the connection terminals 21a and 21b placed on the first support 22, so that the transmitter 10 can be placed directly on the top face of the first support 22 for connection thereof.

The second supports 26a to 26e are implemented as adhesive pads for supporting the second electrode group 24, namely, electrodes Ed1 (+) and Ed3 (+) at the fifth rib position on the left anterior axillary line of the patient PB, electrodes Ed2 (+) and Ed3 (−) at the fifth rib position on the right anterior axillary line of the patient PB, and an electrode EdN on the right lowest rib of the patient PB. Further, the second electrode group 24 is connected to a connection connector 28 via leads 25a, 25b, 25c, 25d, and 25e. The transmitter 10 is provided with a second connection section 12 that can be joined to the connection connector 28, so that the transmitter 10 can be detachably connected to the second electrode group 24 supported by the second supports 26a to 26e via the connection connector 28 and the leads 25a to 25e.

The electrodes Ed1 (−) and Ed1 (+) denote CM5 lead electrodes, Ed2 (−) and Ed2 (+) denote NASA lead electrodes, Ed3 (−) and Ed3 (+) denote CC5 lead electrodes, and EdN denotes a ground electrode. The electrodes can adopt conventionally known body surface electrodes that can be attached directly to the body surface (skin) of the patient PB and are filled with paste made of electrolyte for stably maintaining the space between the skin and each electrode.

Figure 2A:
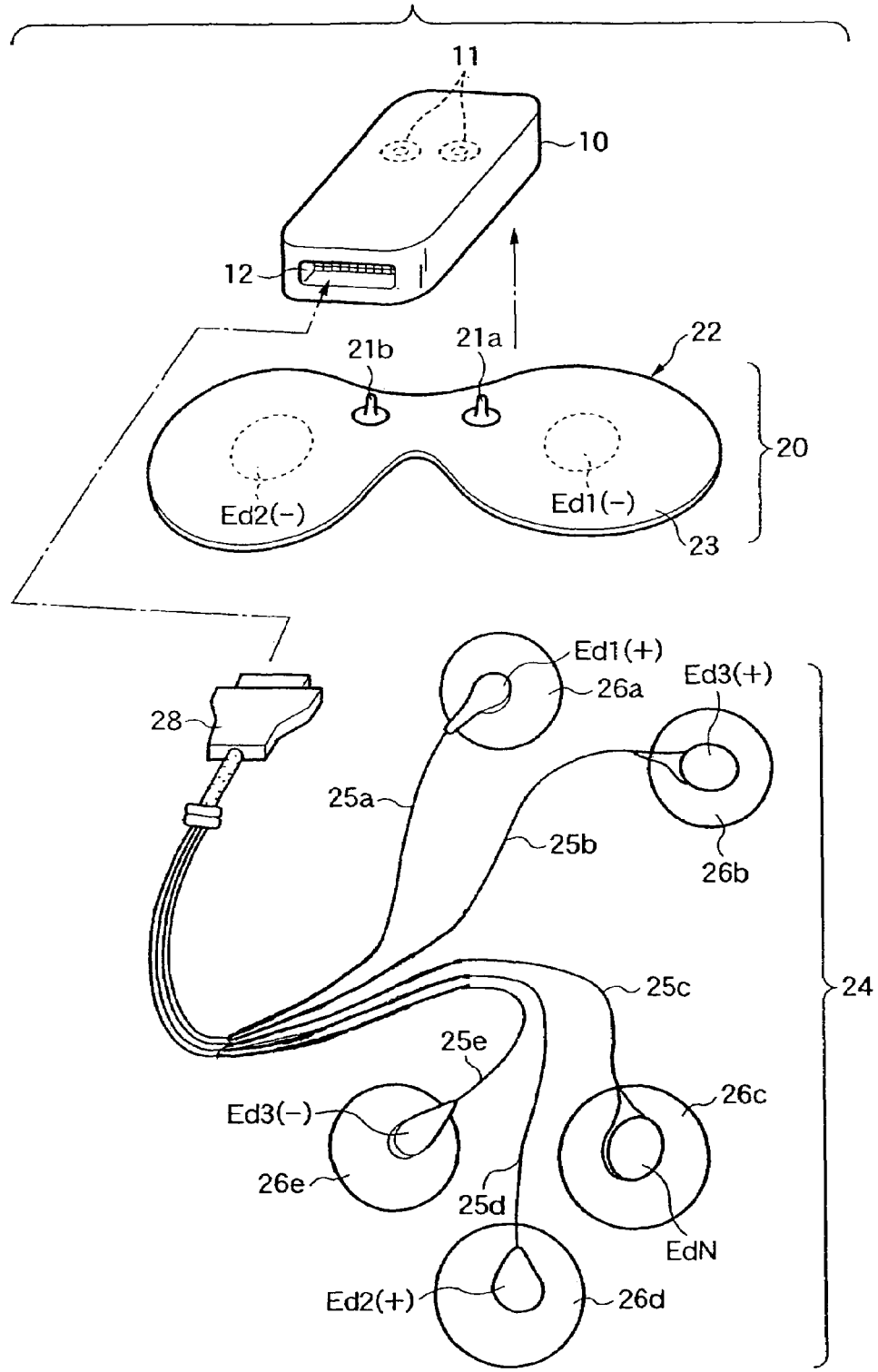
FIG. 2(a) is a schematic perspective view to show the separation state of main components of biological signal detection apparatus for detecting a biological signal shown in FIG. 1.

As a modification of the embodiment shown in FIG. 2(a) as specific joining of the transmitter 10 and the first support 22 and the second supports 26a to 26e, as shown in FIG. 2(b), the transmitter 10 can comprise a first connection section consisting of side clips 13 symmetrically on both sides so as to join to the connection terminals 21a and 21b placed on the first support 22. In this case, each side clip 13 can comprise a clip part 13a1, 13b1 at one end and a knob part 13a2, 13b2 at an opposite end so that the connection terminals 21a and 21b placed on the first support 22 can be detachably joined to the clip parts 13a1 and 13b1 by operating the knob parts 13a2 and 13b2. Other components are identical with those previously described with reference to FIG. 2(a) and are denoted by the same reference numerals in FIG. 2(a) and will not be discussed again in detail.

Next, embodiments concerning the detailed configuration of the transmitter 10 in the biological signal detection apparatus for detecting a biological signal and the communication system which records detected data (electrocardiogram data) and is communicatably connected to the biological signal input apparatus PC implemented as a personal computer, etc., remotely located using a wide area network for inputting the recorded electrocardiogram data to the biological signal input apparatus PC will be discussed.

First Embodiment

Figure 3A:
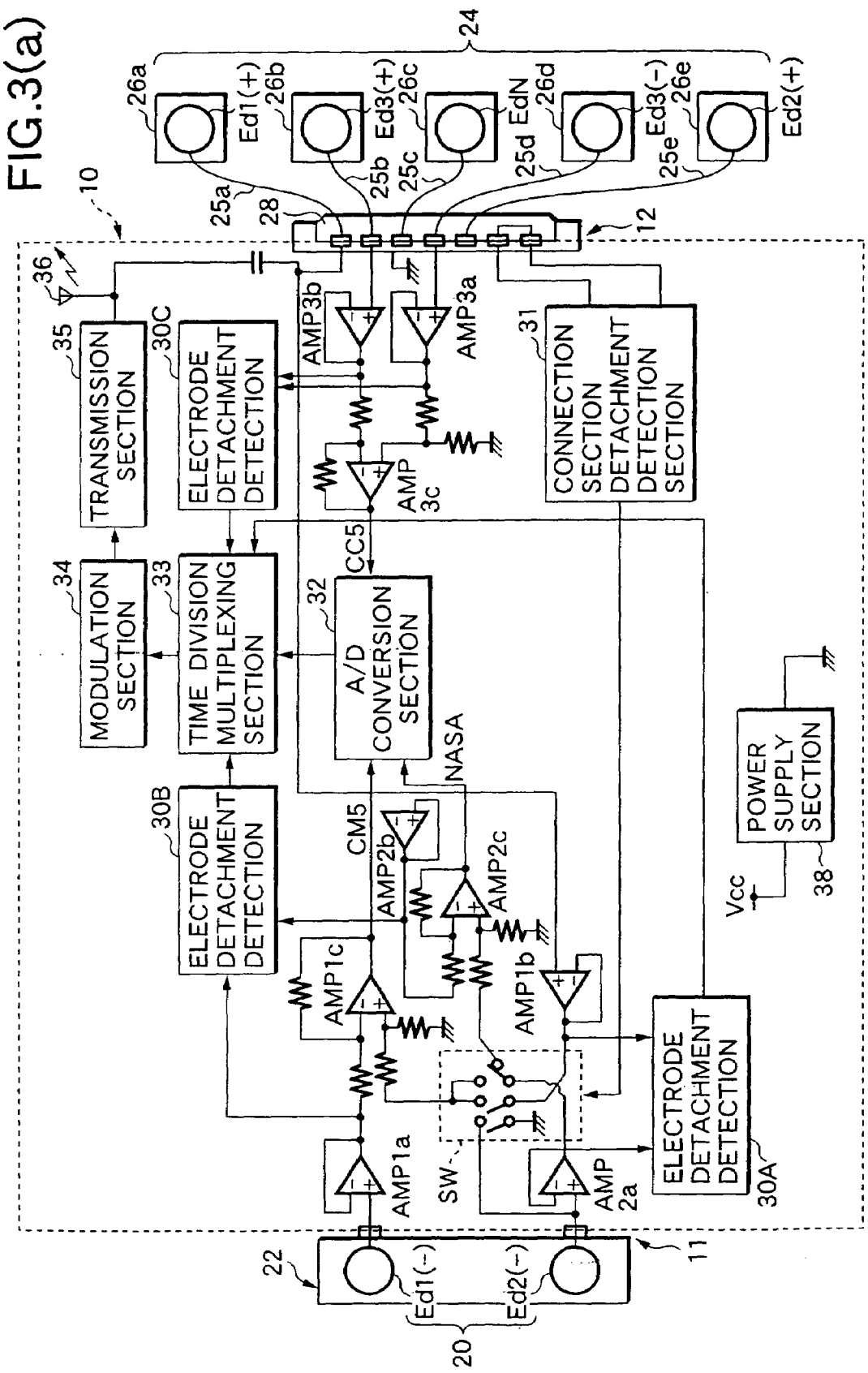
FIG. 3(a) is a schematic block diagram to show a configuration example in the joint state of the biological signal detection apparatus shown in FIGS. 2(a) and 2(b)

FIG. 3(a) shows an embodiment of a transmitter of a biological signal detection apparatus for detecting a biological signal according to the invention. That is, the embodiment is applied to the Holter electrocardiograph shown in FIG. 1, and the circuit configuration of a transmitter 10 of biological signal detection apparatus with a receiver 14 and a recorder 16 attached to the body of a patient PB for use is shown. Components identical with those previously described with reference to FIGS. 1 and 2(a) and(b) are denoted by the same reference numerals in FIG. 3(a) and will not be discussed again in detail.

(1) Configuration of Transmitter as Biological Signal Detection Apparatus

The transmitter 10 as the biological signal detection apparatus shown in FIG. 3(a) is connected to a first electrode group 20 via first connection section 11 and is connected to a second electrode group 24 via a second connection section 12. The transmitter 10 comprises CM5 lead differential amplifiers AMP1a, AMP1b, and AMP1c, NASA lead differential amplifiers AMP2a, AMP2b, and AMP2c, and CC5 lead differential amplifiers AMP3a, AMP3b, and AMP3c connected to CM5 lead electrodes Ed1 (−) and Ed1 (+), NASA lead electrodes Ed2 (−) and Ed2 (+), and CC5 lead electrodes Ed3 (−) and Ed3 (+) set in the first electrode group 20 and the second electrode group 24. A ground electrode EdN-is grounded. Output signals of the differential amplifiers AMP1c, AMP2c, and AMP3c at the last stages of the differential amplifiers are input to an A/D (analog-digital) conversion section 32.

On the other hand, a CM5 lead electrode detachment detector 30A, a NASA lead electrode detachment detector 30B, and a CC5 lead electrode detachment detector 30C are placed in connection circuits of the differential amplifiers, and a connection section detachment detection section 31 is provided for the second connection section 12. Each of the electrode detachment detectors 30A, 30B, and 30C detects an electrode detachment state from the living tissue of the patient PB for each of the electrodes Ed1 (+), Ed3 (+), Ed2 (+), and Ed3 (−) in the second electrode group 24 connected to the second connection section 12, and outputs a detection signal.

The detection signals thus provided by the electrode detachment detectors 30A, 30B, and 30C are input to a time division multiplexing section 33 together with output of the A/D conversion section 32. For a detection signal of the connection section detachment detection section 31, the switch connection operation (described later) is performed for a switch section SW placed between the connection circuits of the differential amplifiers AMP1b and AMP1c and AMP2a and AMP2c on the first connection section 11 side, whereby the potential difference between the electrodes Ed1 (−1) and Ed2 (−) in the first electrode group 20 is detected. Numeral 38 denotes a power supply for supplying power to the sections of the electric circuit.

Further, a real-time biological signal (electrocardiogram data) of the patient PB provided by the time division multiplexing section 33 is modulated by a modulation section 34 together with each electrode detachment detection signal and a connection section detachment signal whenever necessary, and the modulation result is telemetered through a transmission section 35 from a transmission antenna 36 to the outside. The antenna 36 is wired via a capacitor to at least one of terminals connected to leads of the electrodes in the second electrode group 24, for example, the terminal connected to the lead 25a in the transmitter 10, whereby the lead 25a, one of the leads in the second electrode group 24 can be used as an antenna.

Figure 3B:
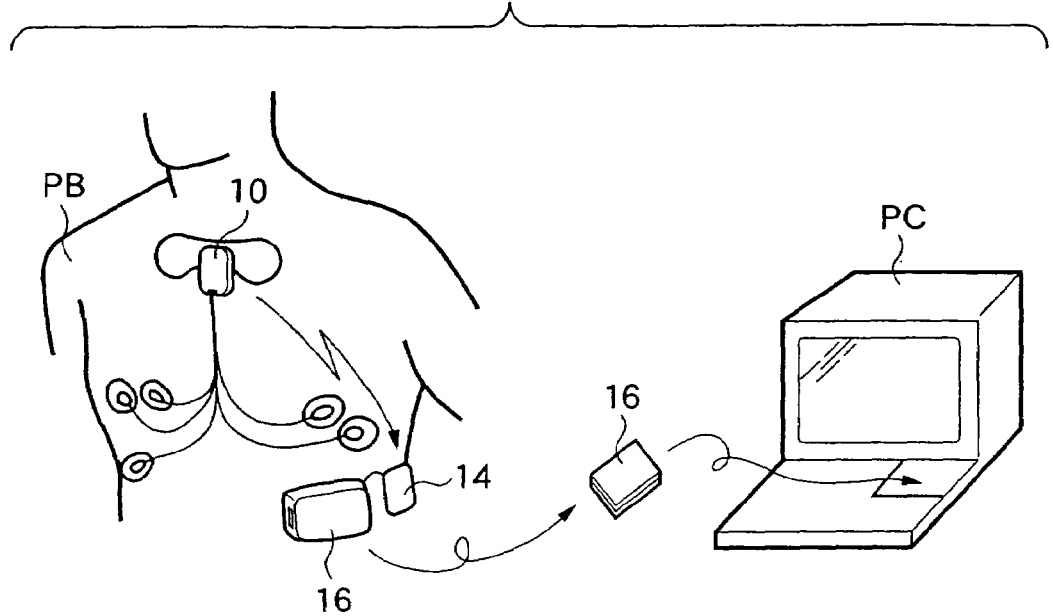
FIG. 3(b) is a schematic representation to show an application example of the biological signal detection apparatus shown in FIG. 3(a) as a Holter electrocardiograph.

As described above, the signal telemetered from the transmitter 10 of the biological signal detection apparatus is recorded in the record section 16 through the receiver 14 attached to the body of the patient PB, as shown in FIG. 3(b). The record section 16 is connected to a personal computer PC, whereby the electrocardiogram data recorded in the record section 16 can be input to the personal computer PC.

(2) Configuration of Receiver 14 as Holter Electrocardiograph

Figure 4:
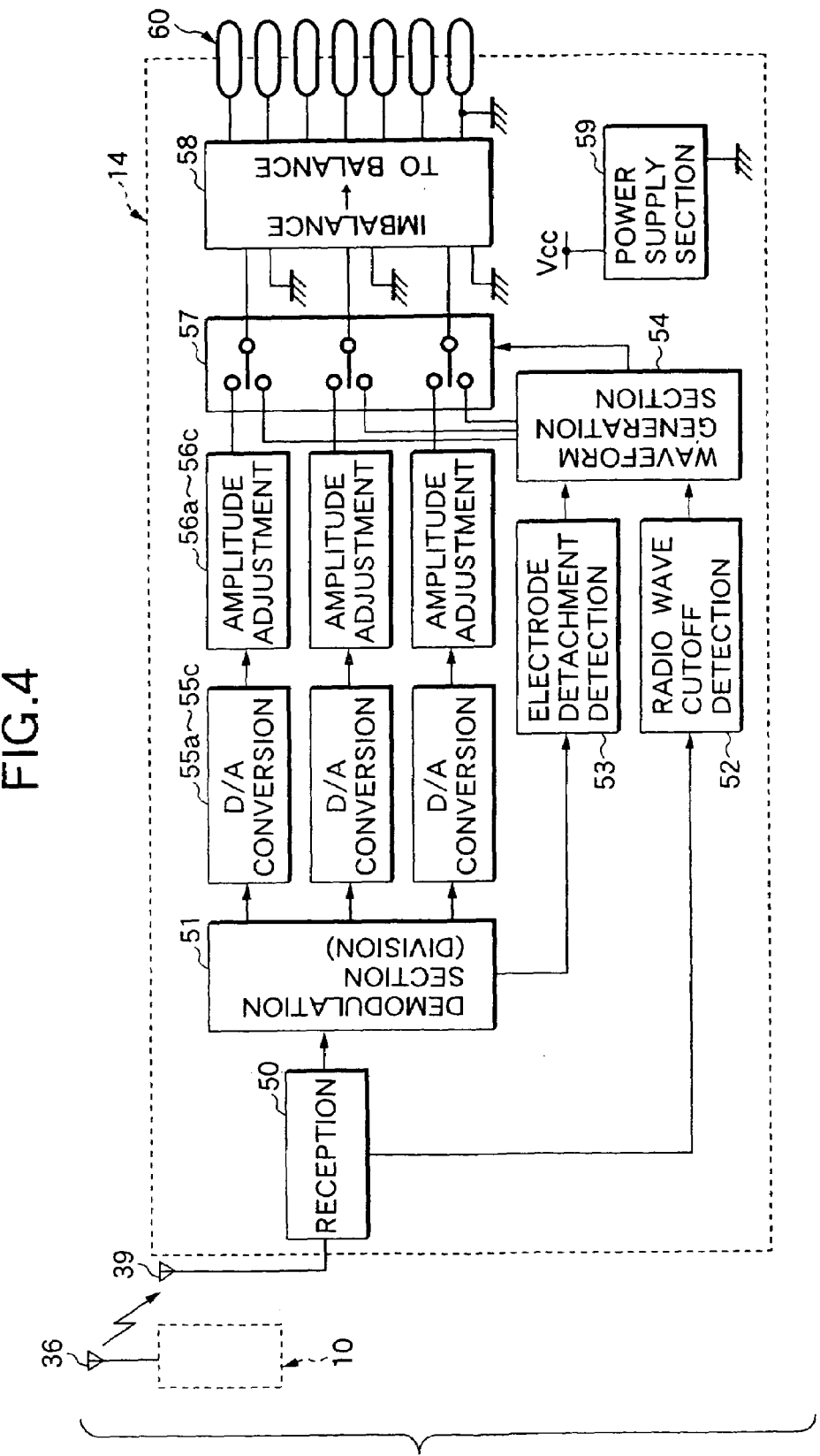
FIG. 4 is a schematic block diagram to show a configuration example of a receiver of a Holter electrocardiograph applied to a communication system of biological signals according to the invention.
Figure 5:
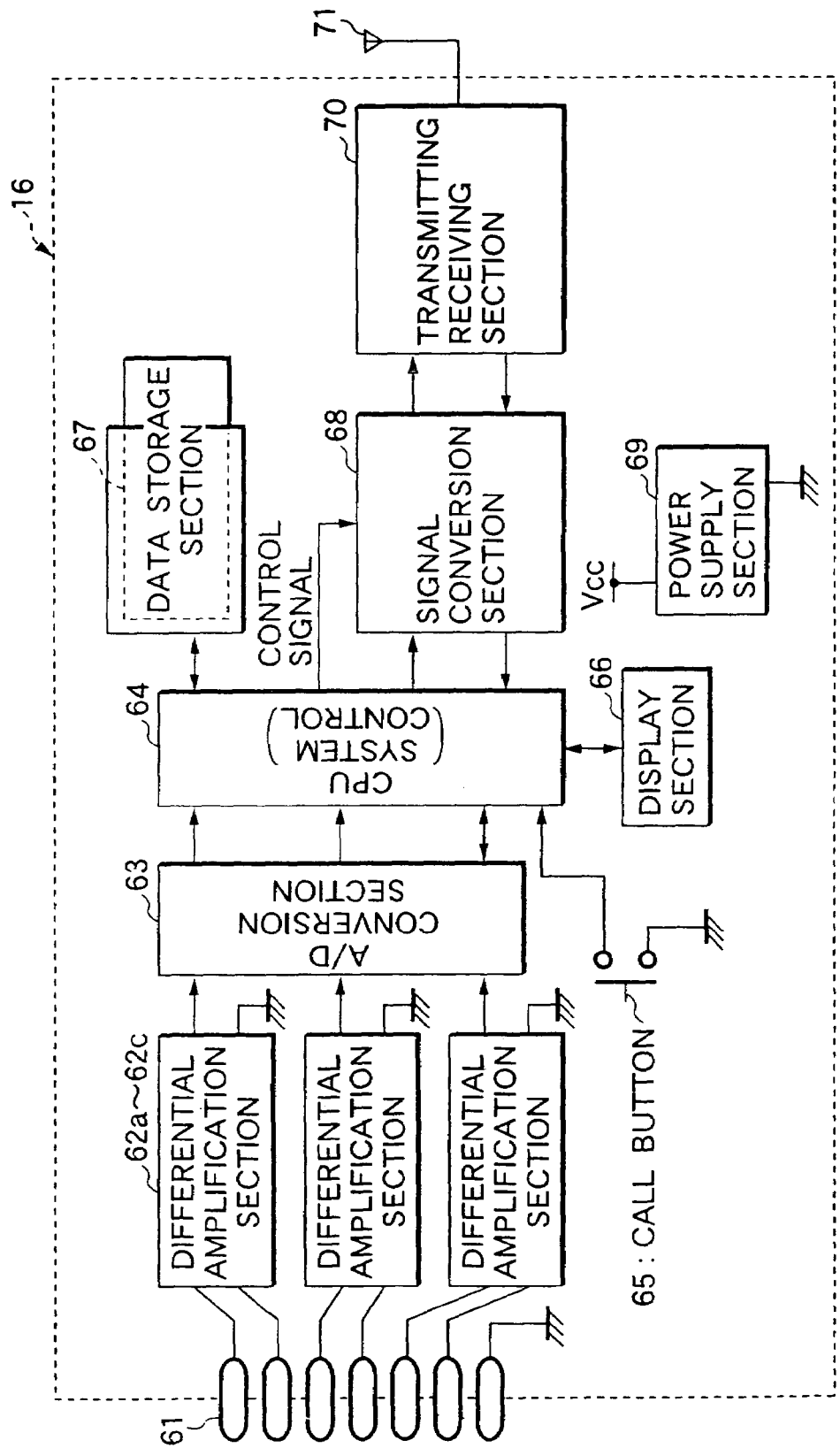
FIG. 5 is a schematic block diagram to show a configuration example of a recorder and a transmitter-receiver of the Holter electrocardiograph applied to the communication system of biological signals according to the invention.

In the embodiment, the receiver 14 and the recorder 16 for receiving and recording an electrocardiogram signal transmitted from the transmitter 10 are configured as shown in FIGS. 4 and 5 respectively.

First, in FIG. 4, the receiver 14 is provided with a reception section 50 and a demodulation section 51 through a reception antenna 39. A radio wave cutoff detector 52 for detecting a radio wave cutoff from the transmitter 10 is connected to the reception section 50 and an electrode detachment detection section 53 for detecting an electrode detachment state signal transmitted from the transmitter 10 is connected to the demodulation section 51. A waveform generation section 54 forms required waveforms of detection signals provided by the radio wave cutoff detector 52 and the electrode detachment detection section 53.

On the other hand, the electrocardiogram signal provided by the demodulation section 51 is appropriately divided and input through D/A (digital-analog) converters 55a to 55c to amplitude adjustment sections 56a to 56c, which then make amplitude adjustment. The electrocardiogram signal thus undergoing the amplitude adjustment is sent via a switch 57 and an imbalance-to-balance converter 58 to an output section connector 60 for connection to an input section connector 61 of the recorder 16 described later so that the electrocardiogram signal and the signal whose waveform is formed accompanying the detection state in the radio wave cutoff detector 52 and the electrode detachment detection section 53 can be output selectively. Numeral 59 denotes a power supply section for supplying power to the sections making up the receiver 14.

(3) Configuration of Recorder 16 and Transmitter-receiver 17 as Holter Electrocardiograph Next, in FIG. 5, in the recorder 16, differential amplification sections 62a to 62c are connected via the input section connector 61 and differentially amplified signals are input through an A/D (analog-digital) conversion section 63 to a CPU (central processing unit) 64 for system control. A call button switch 65, a display section 66, and a data storage section 67 are connected to the CPU 64 and a transmitting and receiving section 70 is also connected via a signal conversion section 68 to the CPU 64. Numeral 69 denotes a power supply section for supplying power to the sections making up the recorder 16. Numeral 71 denotes a transmitting and receiving antenna connected to the transmitting and receiving section 70. For example, the transmitting and receiving antenna 71 is placed as a part of a transmitter-receiver 17 for enabling connection to a wide area network to transmit and receive data and instruction information to and from remotely located biological signal input apparatus PC directly or via a relay transmitter-receiver 19 such as a portable telephone (see FIG. 1).

(4) Configuration of Relay Transmitter-Receiver 19 in Communication System

Figure 6:
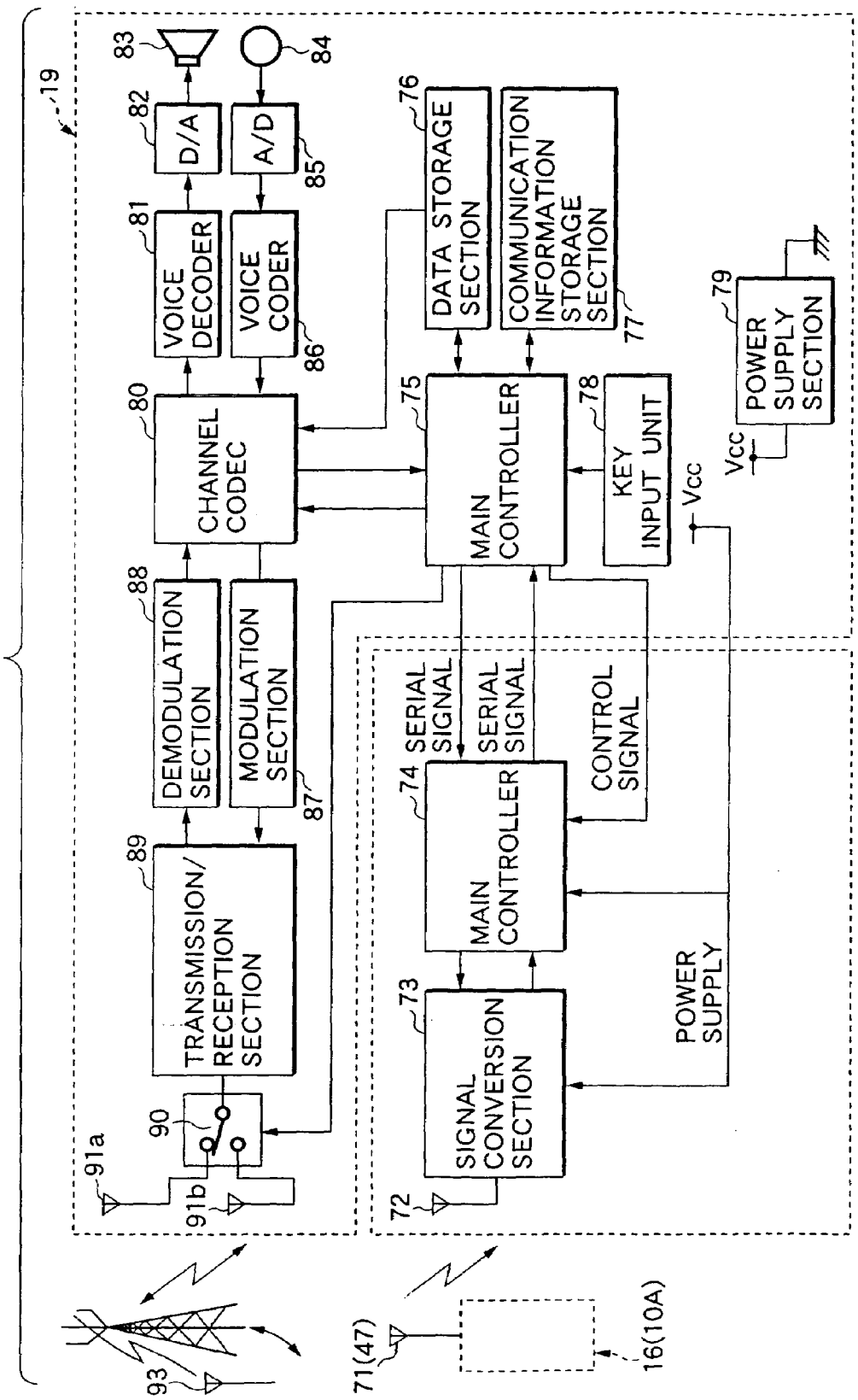
FIG. 6 is a schematic block diagram to show a configuration example of a relay transmitter-receiver for relaying and transmitting/receiving detection data, etc., applied to the communication system of biological signals according to the invention.

Then, FIG. 6 shows the configuration of the relay transmitter-receiver 19 such as a portable telephone for communicating electrocardiogram data recorded in the data storage section 67 of the recorder 16 to the remotely located biological signal input apparatus PC via the wide area network.

That is, in FIG. 6, in the relay transmitter-receiver 19, a transmitting and receiving section 73 and a signal conversion section 74 are connected via a transmitting and receiving antenna 72 connected by telemetering to the transmitting and receiving antenna 71 of the transmitter-receiver 17 (see FIG. 5) placed on the recorder 16. The signal conversion section 74 is connected to a main controller 7,5. The main controller 75 is connected to a data storage section 76, a communication information storage section 77, and a key input unit 78. Further, the main controller 75 and the data storage section 76 are connected to a channel codec 80, and a voice output system consisting of a voice decoder 81, a D/A converter 82, and a speaker 83 and a voice input system consisting of a microphone 84, an A/D converter 85, and a voice coder 86 are placed for inputting and outputting voice from and to the outside through the channel codec 80.

The channel codec 80 is connected to a transmitting and receiving section 89 via a modulation section 87 and a demodulation section 88 and further the transmitting and receiving section 89 is connected switchably to a transmission antenna 91a and a reception antenna 91b via a switch 90 controlled by a signal from the main controller 75. The transmission antenna 91a and the reception antenna 91b are joined to the wide area network connected to the remotely located biological signal input apparatus PC. Numeral 79 denotes a power supply section for supplying power to the sections making up the relay transmitter-receiver 19.

Figure 7:
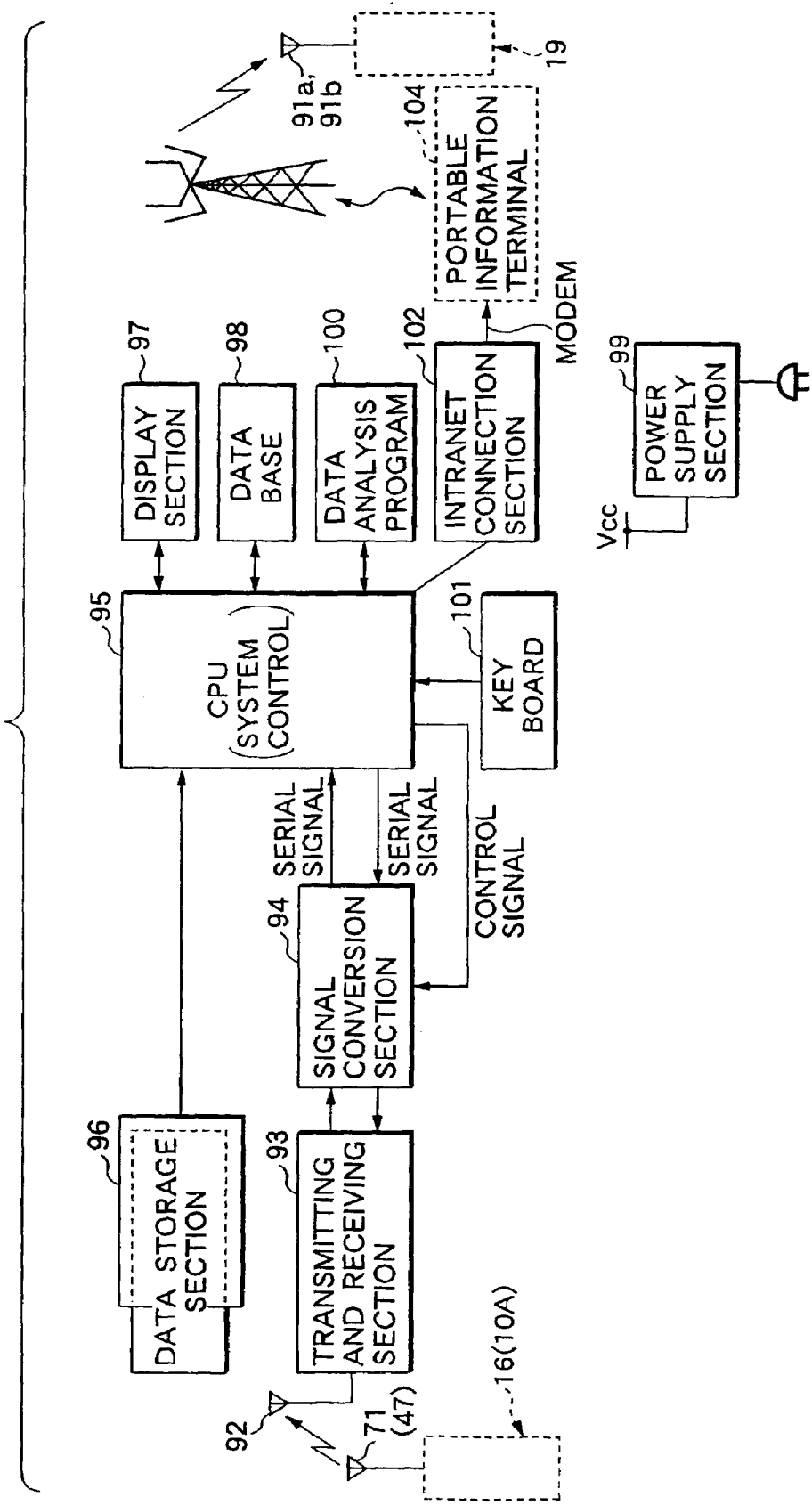
FIG. 7 is a schematic block diagram to show a configuration example of a biological signal input apparatus for receiving and recording detection data, etc., and transmitting instruction information, applied to the communication system of biological signals according to the invention.

(5) Configuration of Biological Signal Input Apparatus PC in Communication System FIG. 7 shows the configuration of the biological signal input apparatus PC implemented as a personal computer, etc., that can communicate electrocardiogram data recorded in the data storage section 67 of the recorder 16 by connecting the transmitting and receiving antenna 71 of the transmitter-receiver 17 (see FIG. 5) of the recorder 16 and the remotely located biological signal input apparatus PC directly or with the relay transmitter-receiver 19 of a portable telephone, etc., (see FIG. 6) through the wide area network.

That is, in FIG. 7, in the biological signal input apparatus PC, a transmitting and receiving section 93 and a signal converter 94 are connected via a transmitting and receiving antenna 92 for directly connecting by telemetering to the transmitter-receiver 17 (see FIG. 5) of the recorder 16. The signal converter 94 is connected to a CPU 95 for system control. The CPU 95 is connected to a data storage section 96, a display section 97, a database 98, a data analysis program 100, and a keyboard 101. Numeral 99 denotes a power supply section for supplying power to the sections making up the biological signal input apparatus PC. An intranet connection section 102 is provided for the system control CPU 95 of the biological signal input apparatus PC and the biological signal input apparatus PC is connected through the intranet connection section 102 to the transmission antenna 91a and the reception antenna 91b (see FIG. 6) of the relay transmitter-receiver 19 of a portable telephone, etc., (see FIG. 6) by the wide area network.

(6) General System Configuration and Operation Flow of Communication System

Figure 8:
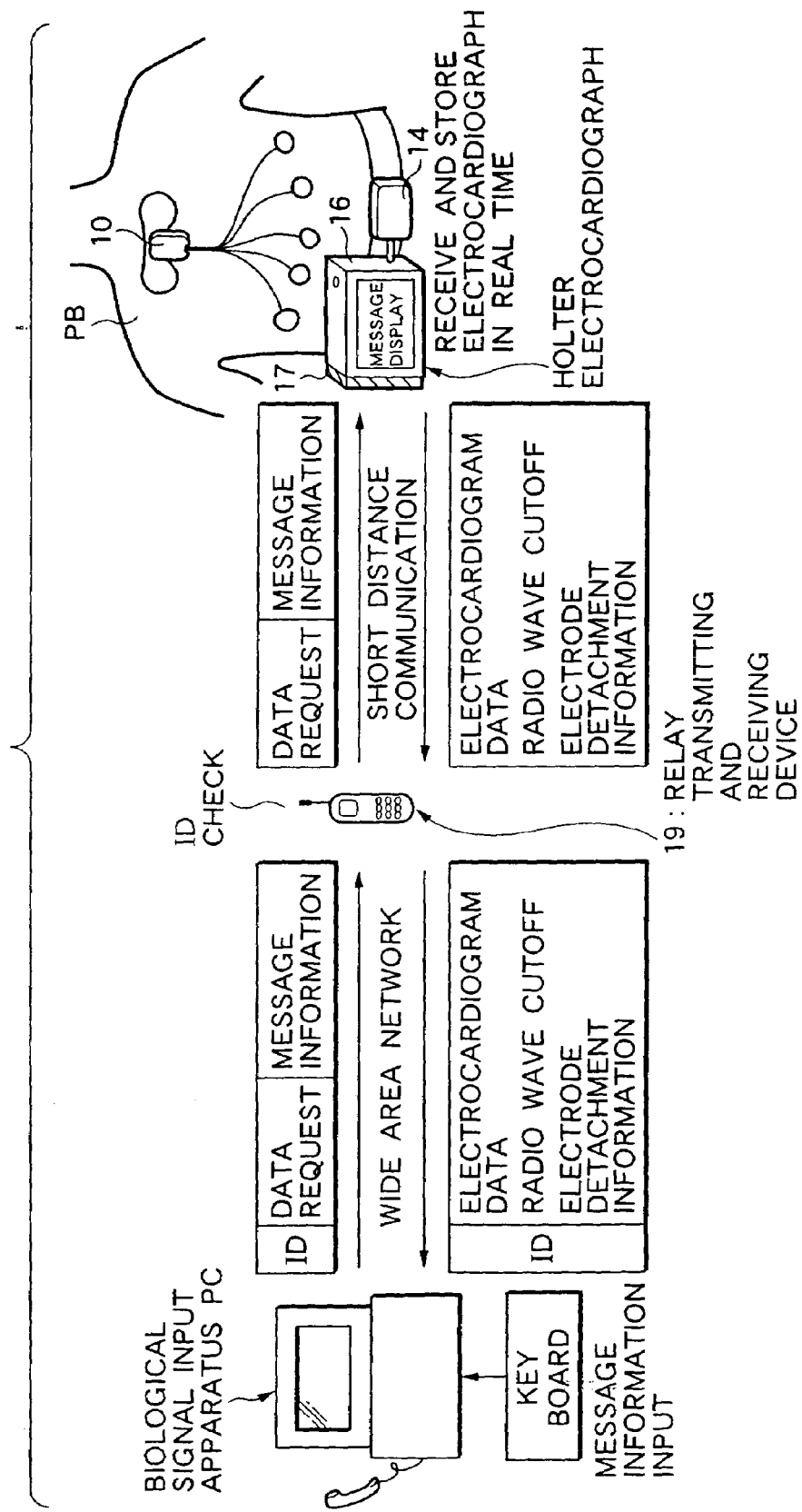
FIG. 8 is a schematic representation to show one embodiment of a flow of data and information in the communication system of biological signals according to the invention.

Therefore, the general system configuration of the communication system in the embodiment can be provided as shown in FIG. 8. In this case, an operation flow can be set as shown in FIG. 9.

That is, according the communication system configuration shown in FIG. 8, the electrocardiogram data recorded in the recorder 16 of the Holter electrocardiograph can be communicated with the biological signal input apparatus PC about inputting the electrocardiogram data etc. together with instruction information (message information) over the wide area network through the transmitter-receiver 17 of the Holter electrocardiograph and the relay transmitter-receiver 19.

Figure 9:
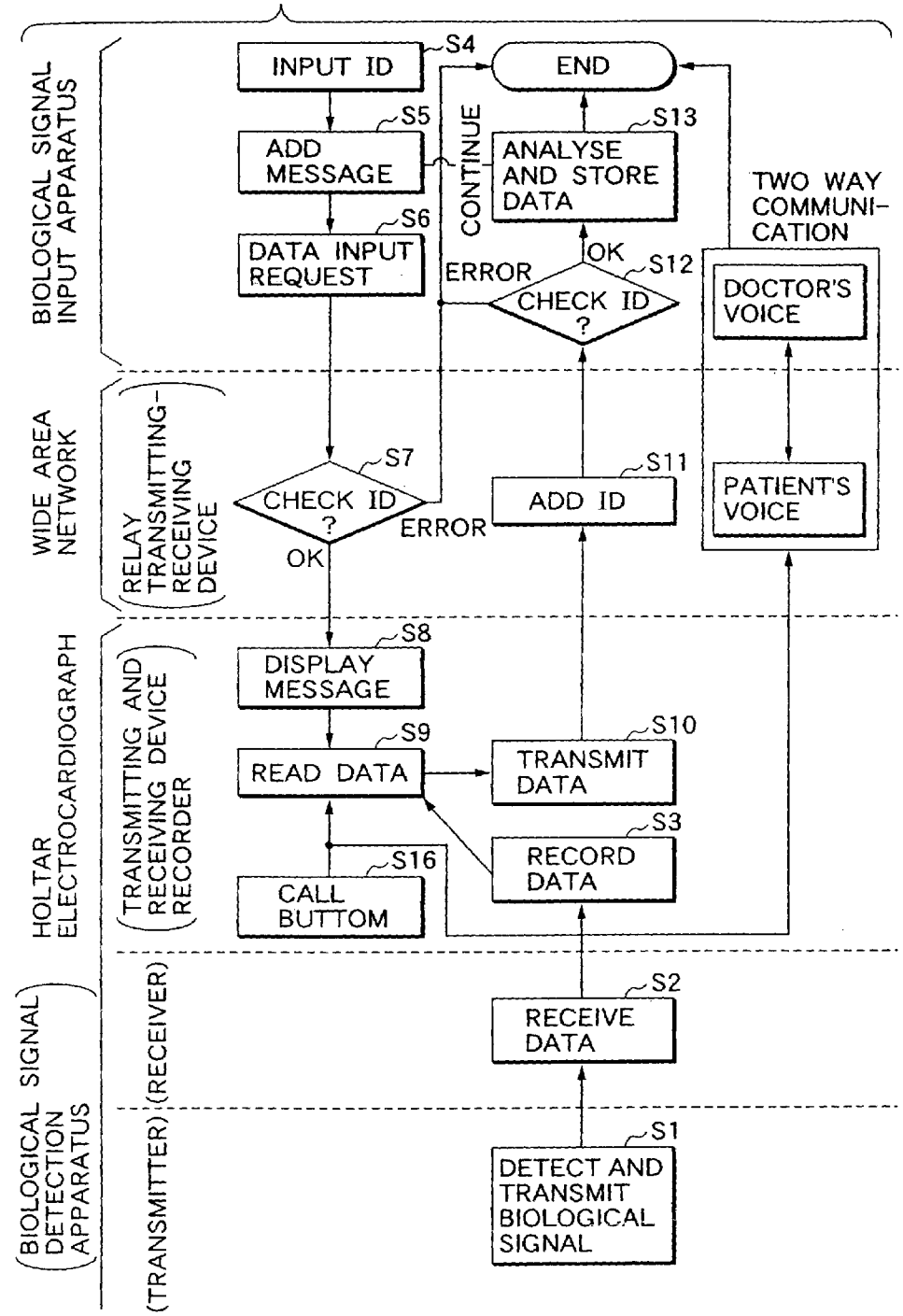
FIG. 9 is a flowchart to describe the operation of the communication system according to the invention shown in FIG. 8.

In this case, in the operation flow, as shown in FIG. 9, in the Holter electrocardiograph, a biological signal (electrocardiogram data) is detected and transmitted in the transmitter 10 of the biological signal detection apparatus at step S1. Next, in the receiver 14, the detection signal transmitted from the transmitter 10 is received at step S2 and is recorded as electrocardiogram data in the data storage section 67 of the recorder 16 at step S3. Then, in the biological signal input apparatus PC, the ID (identification label) of the patient is input at step S4, next instruction information (message) is added at step S5 and a data input request instruction is given at step S6. The data input request instruction thus given is transmitted to the Holter electrocardiograph via the wide area network (relay transmitter-receiver 19). In this case, in the relay transmitter-receiver 19, the ID is checked for validity at step S7 and if the ID is valid, the contents of the instruction information are displayed on the recorder. 16 of the Holter electrocardiograph at step S8, the required electrocardiogram data recorded in the data storage section 67 is read at step S9 and is transmitted to the biological signal input apparatus PC over the wide area network (relay transmitter-receiver 19) through the transmitter-receiver 17 consisting of the transmitting and receiving section 70 and the transmitting and receiving antenna 71 at step S10. At this time, the ID of the patient is added to the electrocardiogram data at step S11 and is checked for validity in the biological signal input apparatus PC at step S12. If the ID is valid, the data is analyzed by the data analysis program 100 and is recorded in the data storage section 96 at step S13. If the patient PB to whom the Holter electrocardiograph is attached makes a request for conversation with a doctor on the biological signal input apparatus PC side, the patient can operate the call button switch 65 of the recorder 16, so that they can converse with each other using the wide area network.

Second Embodiment

Figure 10:
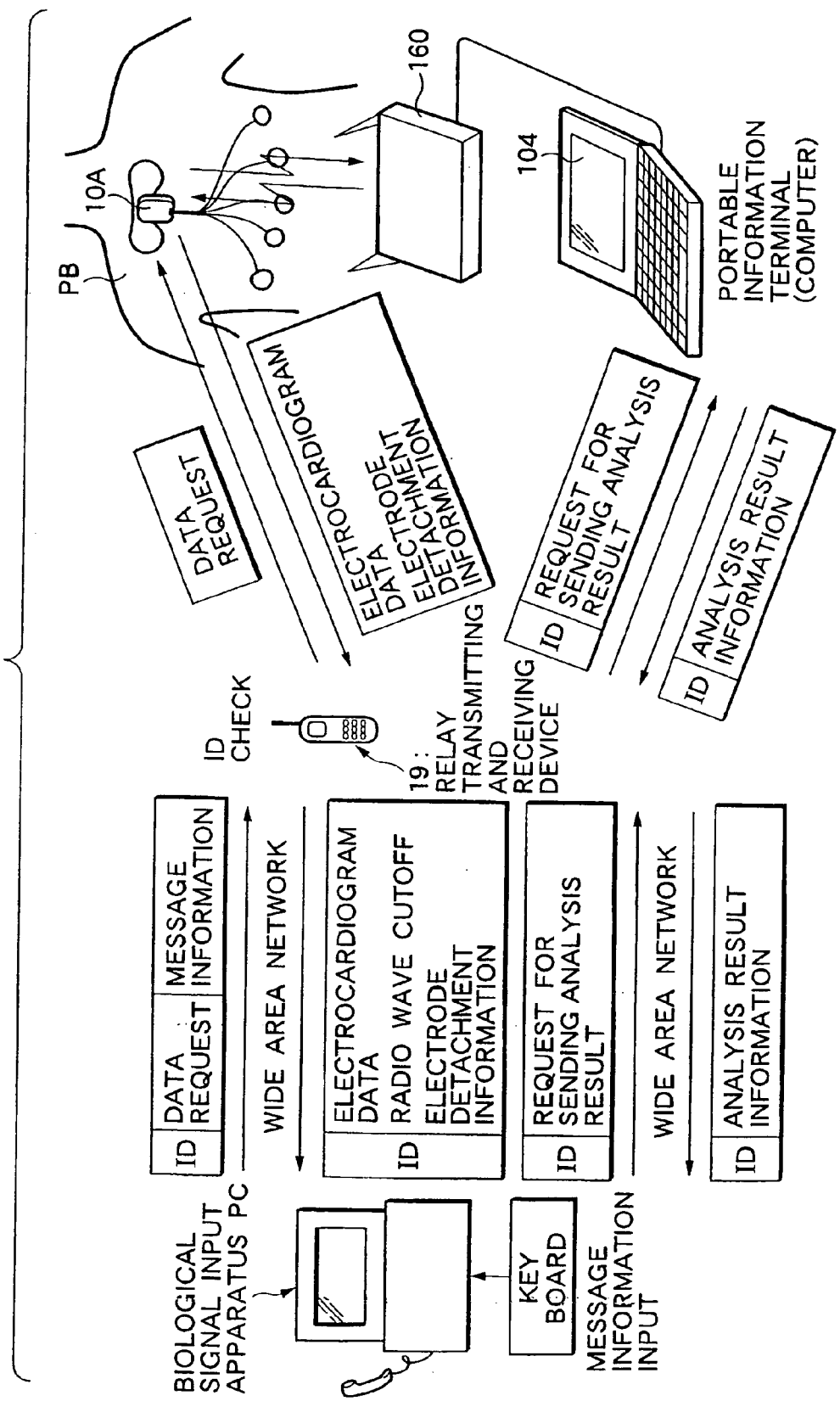
FIG. 10 is a schematic representation to show another embodiment of a flow of data and information in communication system of biological signals according to the invention.

FIG. 10 shows another embodiment of transmitter of biological signal detection apparatus for detecting a biological signal according to the invention. That is, in the embodiment, a data storage section and a transmitting and receiving section are contained in the transmitter of the biological signal detection apparatus in the first embodiment to form a transmitter-receiver 10A, and as a communication system, the transmitter-receiver 10A is communicatably connected to a biological signal input apparatus PC implemented as a remotely located personal computer, etc., directly or via a relay transmitter-receiver 19 of a portable telephone, etc., using a wide area network, whereby electrocardiogram data recorded in the data storage section is input to the biological signal input apparatus PC. Of course, as shown in FIG. 10, the transmitter-receiver 10A is communicatably connected to the biological signal input apparatus PC via a receiver 160 to input electrocardiogram data recorded in the data storage section to the biological signal input apparatus PC.

(1) Configuration of Transmitter-receiver as Biological Signal Detection Apparatus Therefore, the transmitter-receiver 10A as the biological signal detection apparatus in the embodiment can adopt the circuit configuration as shown in FIG. 11(a). Components identical with those previously described with reference to FIG. 3(a) are denoted by the same reference numerals in FIG. 11(a) and will not be discussed again in detail.

Figure 11B:
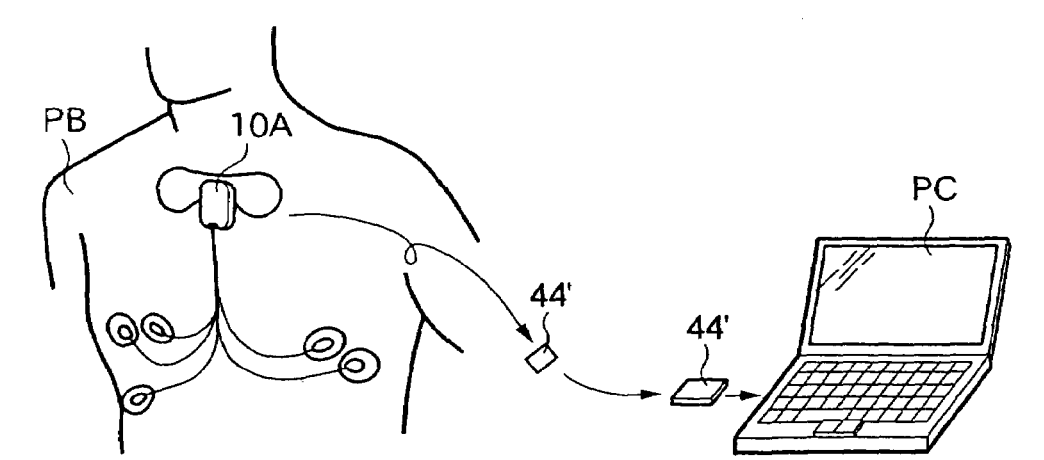
FIG. 11(b) is a schematic representation to show another application example of the biological signal detection apparatus according to the invention as a Holter electrocardiograph.

That is, in FIG. 11(a), in the embodiment, a CPU 40 is provided in place of the time division multiplexing section 33 in the first embodiment. In the CPU 40, based on time data 41 and an operation program set in a memory section 42 consisting of ROM and RAM, detection signals of electrode detachment detectors 30A, 30B, and 30C and output of an A/D converter 32 are input and required electrocardiogram data is input to and recorded in a data storage section 43. The data signal recorded in the data storage section 43 is modulated by a modulation section 44 and is telemetered to the outside via a transmitting and receiving section 46 and a transmitting and receiving antenna 47 and a signal received from the outside via the transmitting and receiving antenna 47 and the transmitting and receiving section 46 is demodulated by a demodulation section 45 and is input to the CPU 46. Further, as shown in FIG. 11(b), detachable storage means 44, such as a memory card is placed in the data storage section of the transmitter-receiver 10A and is connected to a personal computer PC, whereby electrocardiogram data recorded in the storage means 44' could input to the personal computer PC.

Using the biological signal detection apparatus of the embodiment described above, the transmitter-receiver 10A of the biological signal detection apparatus is connected to a remotely located personal computer PC over a wide area network of telephone lines, etc., via the relay transmitter-receiver such as a portable telephone, whereby electrocardiogram data and instruction information of conversation, etc., can be transferred between a patient and a doctor.

(2) Configuration of Relay Transmitter-receiver 19 and Biological Signal Input Apparatus PC in Communication System In the embodiment, the electrocardiogram data detected and recorded in the transmitter-receiver 10A of the biological signal detection apparatus is communicated with the remotely located biological signal input apparatus PC over the wide area network directly by the transmitter-receiver 10A or via the relay transmitter-receiver 19 of a portable telephone, etc., not via the receiver 14, the recorder 16, or the transmitter-receiver 17 as the Holter electrocardiograph in the first embodiment, whereby the electrocardiogram data and instruction information of conversation, etc., can be transferred between a patient and a doctor. Therefore, in the embodiment, the receiver 14 (see FIG. 4), the recorder 16, and the transmitter-receiver 17 (see FIG. 5) as the Holter electrocardiograph can be omitted. In the embodiment, the relay transmitter-receiver 19 (see FIG. 6) and the biological signal input apparatus PC (see FIG. 7) described in the first embodiment can be used as they area.

With the relay transmitter-receiver 19 (see FIG. 6) used in the second embodiment, data or instruction information transferred to and from a transmitting and receiving section 73 via a transmitting and receiving antenna 72 is transferred to and from the transmitting and receiving antenna 47 of the transmitter-receiver 10A as the biological signal detection apparatus shown in FIG. 1(a). Likewise, with the biological signal input apparatus PC (see FIG. 7) used in the embodiment, data or instruction information transferred to and from a transmitting and receiving section 93 via a transmitting and receiving antenna 92 is also transferred to and from the transmitting and receiving antenna 47 of the transmitter-receiver 10A as the biological signal detection apparatus shown in FIG. 11(a).

(3) General System Configuration and Operation Flow of Communication System

The general system configuration of the communication system in the embodiment can be provided as shown in FIG. 10. In this case, an operation flow can be set as shown in FIGS. 12 and 13.

That is, according the communication system configuration shown in FIG. 10, as the basic operation, the electrocardiogram data recorded in the data storage section 43 of the transmitter-receiver 10A in the biological signal detection apparatus as the Holter electrocardiograph can be communicated with the biological signal input apparatus PC about inputting the cardiogram data etc. together with instruction information (message information) over the wide area network through the transmitter-receiver 10A and the relay transmitter-receiver 19.

If the patient PB to whom the Holter electrocardiograph is attached requests a doctor on the biological signal input apparatus PC side to disclose information concerning the data analysis result, etc., a portable information terminal 104 is communicatably connected to the relay transmitter-receiver 19 connected to the wide area network, whereby communications with the biological signal input apparatus PC can be conducted.

Figure 12:
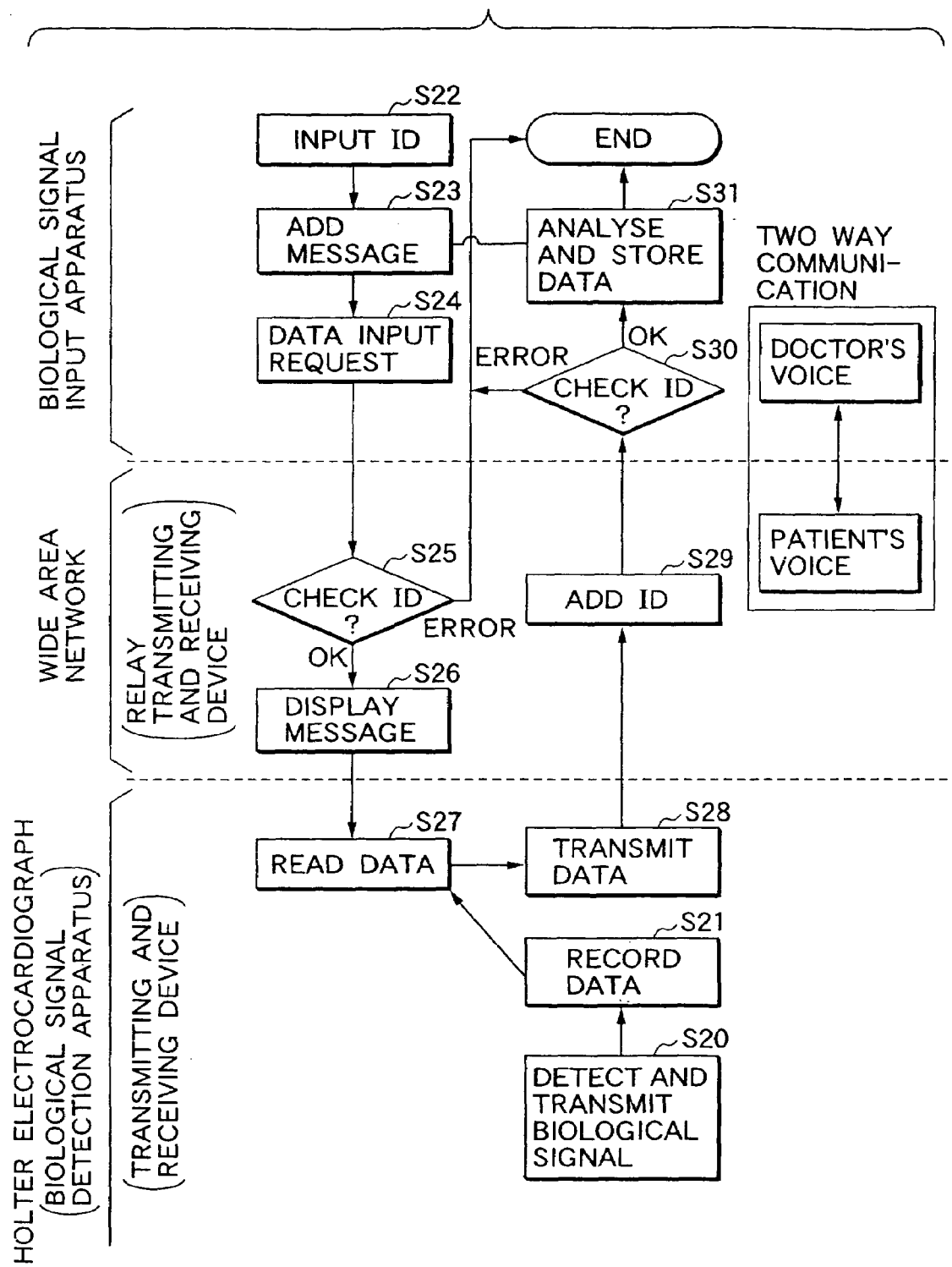
FIG. 12 is a flowchart to describe the basic operation of the communication system according to the invention shown in FIG. 10.
Figure 13:
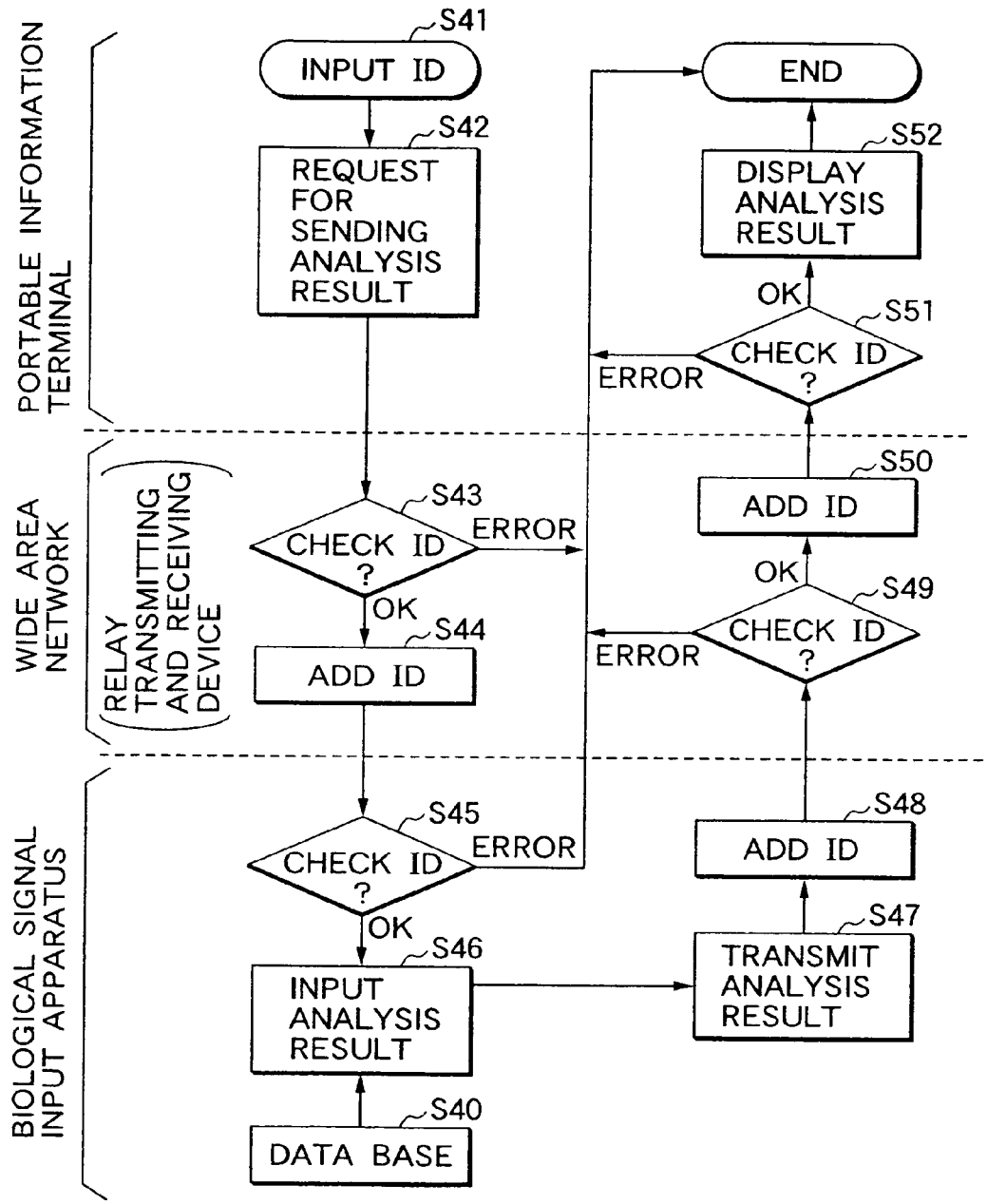
FIG. 13 is a flowchart to describe another operation of the communication system according to the invention shown in FIG. 10.

Then, in the basic operation flow of the communication system in the embodiment, as shown in FIG. 12, in the Holter electrocardiograph, a biological signal (electrocardiogram data) is detected in the transmitter-receiver 10A of the biological signal detection apparatus at step S20 and is recorded as electrocardiogram data in the data storage section 67 at step S21. Then, in the biological signal input apparatus PC, the ID (identification label) of the patient is input at step S22, next instruction information (message) is added at step S23 and a data input request instruction is given at step S24. The data input request instruction thus given is transmitted to the Holter electrocardiograph via the wide area network (relay transmitter-receiver 19). In this case, in the relay transmitter-receiver 19, the ID is checked for validity at step S25 and if the ID is valid, the contents of the instruction information are displayed on the relay transmitter-receiver 19 at step S26, the required electrocardiogram data recorded in the data storage section 67 of the transmitter-receiver 10A is read at step S27 and is transmitted to the biological signal input apparatus PC over the wide area network (relay transmitter-receiver 19) through the transmitting and receiving section 46 and the transmitting and receiving antenna 47 at step S28. At this time, the ID of the patient is added to the electrocardiogram data at step S29 and is checked for validity in the biological signal input apparatus PC at step S30. If the ID is valid, the data is analyzed by a data analysis program 100 and is recorded in a data storage section 96 at step S31. If the patient PB to whom the Holter electrocardiograph is attached makes a request for conversation with a doctor on the biological signal input apparatus PC side, the patient can operate the relay transmitter-receiver 19 of the recorder 16, so that they can converse with each other using the wide area network.

If the patient PB to whom the Holter electrocardiograph is attached requests the doctor on the biological signal input apparatus PC side to disclose information concerning the data analysis result, etc., the operation flow is as follows: As shown in FIG. 13, first in the biological signal input apparatus PC, record data is input based on a data request signal and the analysis result of the record data is prepared and is stored in a database 98 at step S40. Then, in the portable information terminal 104, the ID (identification label) of the patient is input at step S41, next a request for sending the data analysis result is made at step S42. The request for sending the data analysis result is transmitted to the biological signal input apparatus PC via the wide area network (relay transmitter-receiver 19). In this case, in the relay transmitter-receiver 19, the ID is checked for validity at step S43 and if the ID is valid, the ID is added at step S44 and is checked for validity in the biological signal input apparatus PC at step S45 and the required analysis result stored in the database is input at step S46 and is transmitted with the ID added over the wide area network (relay transmitter-receiver 19) to the portable information terminal 104 at steps S47 and S48. In this case, in the relay transmitter-receiver 19, the ID is checked for validity at step S49 and if the ID is valid, the ID is added at step S50 and is received at the portable information terminal 104. Also in the portable information terminal 104, the ID is checked for validity at step S51 and if the ID is valid, the received data analysis result can be displayed on a display section of the portable information terminal 104 at step S52.

Next, in the second connection section 12 in the biological signal detection apparatus adopting the configuration described above, the operation of the connection section detachment detector 31 and the switch SW and the biological signal detection operation in a normal connection state will be discussed with reference to FIG. 14 and the operation of the connection section detachment detector 31 and the switch SW and the biological signal detection operation in a connection section detachment state will be discussed with reference to FIG. 15. Components identical with those previously described with reference to FIGS. 3 and 11 are denoted by the same reference numerals in FIGS. 14 an 15 and will not be discussed again in detail.

Operation in Normal Connection State

Figure 14:
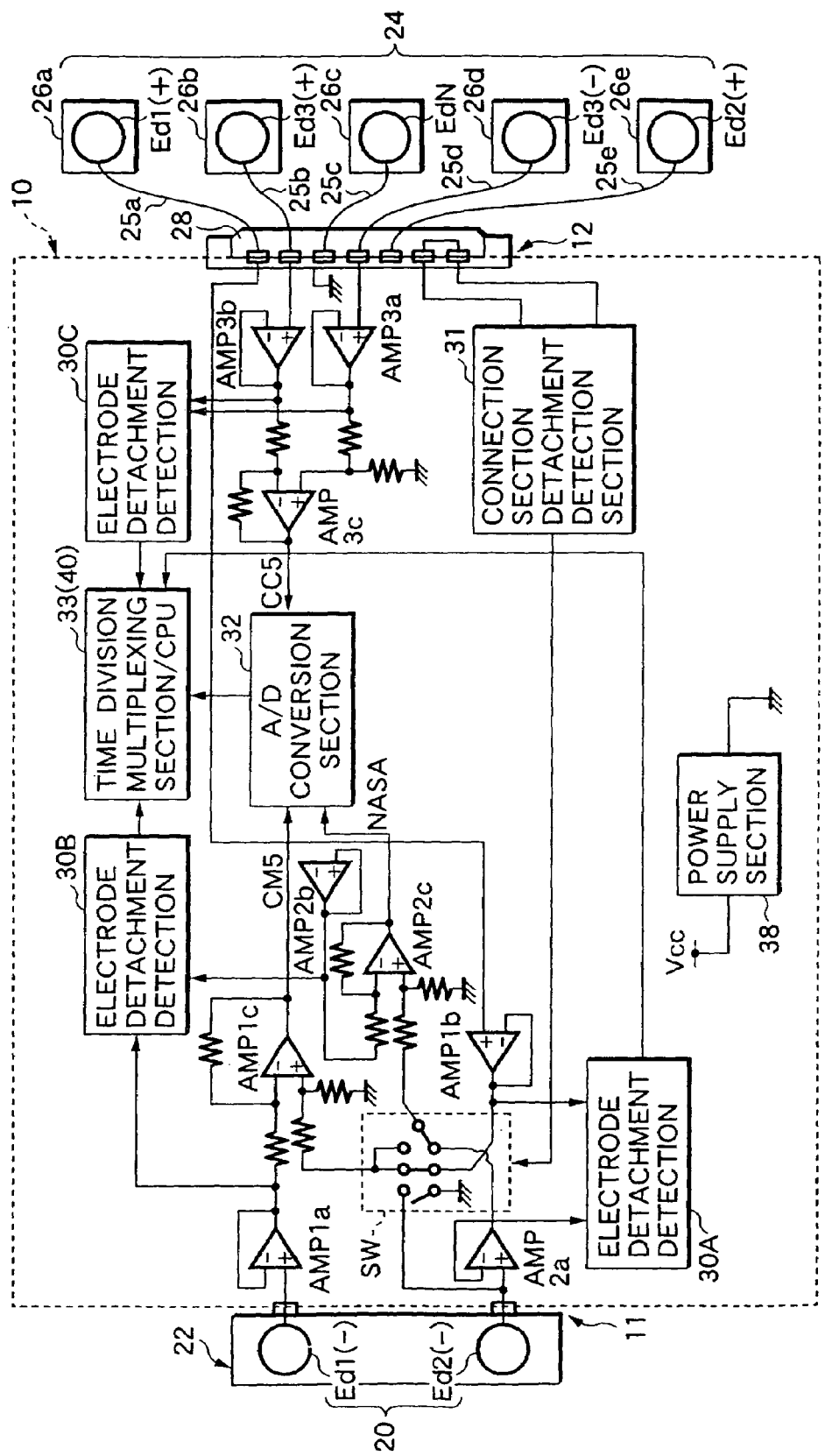
FIG. 14 is a block diagram to describe the operation in an electrode detachment detection state in the communication system of biological signals according to the invention.

When the first connection section 11 and the second connection section 12 and the transmitter 10 are in the normal connection state, the contacts of the switch SW are placed in a connection state, as shown in FIG. 14. That is, the differential amplifiers AMP1$b$ and AMP1$c$ (CM5 lead) are placed in a connection state and the differential amplifiers AMP2$a$ and AMP2$c$ (NASA lead) are placed in a connection state. Consequently, the CM5 lead differential amplifiers AMP1$a$, AMP1$b$, and AMP1$c$, the NASA lead differential amplifiers AMP2$a$, AMP2$b$, and AMP2$c$, and the CC5 lead differential amplifiers AMP3$a$, AMP3$b$, and AMP3$c$ are properly brought into conduction unless electrode detachment is not detected in the electrode detachment detector 30A, 30B, or 30C, whereby required biological signal can be provided in the A/D conversion section 32.

Operation in Connection Section Detachment State

When a connection section detachment state is entered in the second connection section 12 and the transmitter 10 as shown in FIG. 15, the connection section detachment detector 31 detects this state and switches the contacts of the switch SW in connection. That is, the differential amplifiers AMP1$b$ and AMP1$c$ (CM5 lead) are disconnected and the connection of the differential amplifiers AMP2$a$ and AMP2$c$ (NASA lead) is switched to connection of the differential amplifiers AMP2$a$ and AMP1$c$ and a part of the input side connection circuit of the differential amplifier AMP2$a$ is grounded. Consequently, the potential difference between the electrodes Ed1 (−) and Ed2 (−) in the first electrode group 20 can be provided in the A/D conversion section 32. That is, an electrocardiogram waveform sufficient for detecting a heart rate can be provided by measuring the potential difference.

Although the invention has been described in its preferred embodiments, it is understood that the invention is not limited to the specific embodiments thereof and, for example, the configurations of the supports of the electrodes of the biological signal detection apparatus shown in FIGS. 2 and 3 and the configuration and placement of the connection sections can be changed in design in various manners and other configurations can also be changed in design in various manners without departing from the spirit and the scope of the invention.

As seen from the described configuration, according to the apparatus of the invention, the first electrode group is supported collectively on a single support, whereby the number of attached electrodes can be decreased and the attachment work is facilitated. That is, according to the invention, one-touch attachment is enabled and the attachment speed can be increased. Thus, in the apparatus of the invention, a simple electrocardiogram waveform can be measured and moreover the potential difference between the electrodes by CM5 lead, etc., can be measured simply by fitting an electrocardiograph electrode code into the second connection section f,or the second electrode group without changing electrode attachment. For example, in the apparatus of the invention, for a patient requiring a first aid, first a simple electrocardiogram is measured by the transmitter comprising the first electrode group and the transmitter in one piece, then if the conditions of the patient become calm and a long-term or accurate electrocardiogram waveform(CM5 lead) becomes necessary, an electrocardiogram waveform can be easily led simply by connecting the second electrode group to the second connection section without changing electrode attachment.

As seen from the described embodiments, the biological signal detection apparatus according to the invention comprises a first electrode group for detecting a biological signal, a first support being attached to the living tissue surface of a patient for supporting the first electrode group, a second electrode group for detecting a biological signal, a second support being attached to the living tissue surface for supporting the second electrode group, and a transmitter comprising an electric circuit for processing the signals detected by the first and second electrode groups and telemetering the detected signals, the transmitter comprising a first connection section for electrically connecting the first electrode group to the transmitter and fixing the transmitter directly onto the first support and a second connection section for electrically connecting signal lines from the second electrode group to the transmitter. Thus, a large number of excellent advantages can be provided such that a medical telemetry system that can eliminate inconvenience or discomfort when the electrodes are attached to a patient and can prevent detachment of an electrode from causing a malfunction to occur and smoothly and simply exchange information between a patient and a monitor can be constructed. The described biological signal detection apparatus according to the invention can be applied to easily provide an easy-to-handle Holter electrocardiograph which enables the user to properly and promptly monitor electrocardiogram data of a patient.

As seen from the described embodiments, the communication system of biological signals according to the invention comprises a Holter electrocardiograph comprising a biological signal detection apparatus comprising a plurality of electrodes for detecting a biological signal, supports being attached to the living tissue surface of a patient for supporting the electrodes, and a transmitter for processing the signal detected by the electrode and telemetering the detected signal, a receiver for receiving the signal telemetered from the transmitter of the biological signal detection apparatus and demodulating the received signal, the receiver comprising a terminal for outputting the demodulated signal to a biological signal input section of required record means, and a recorder comprising record means for recording the demodulated signal output from the terminal of the receiver, wherein the recorder of the Holter electrocardiograph comprises transmitting and receiving means for telemetering the signal stored in the record means, receiving an external transmission signal, and telemetering some or all of the signals stored in the record means as instructed by the external transmission signal, and a biological signal input apparatus comprising transmitting and receiving means for inputting signals and transmitting and receiving communication information to and from the transmitting and receiving means of the recorder of the Holter electrocardiograph through a relay transmitter-receiver and a wide area network is provided. Thus, a large number of excellent advantages can be provided such that a medical telemetry system that can prevent detachment of an electrode from causing a malfunction to occur and can smoothly and simply exchange information between a patient and a monitor can be constructed.

Particularly, according to the communication system of the invention adopting the configuration described above, if instruction information including a request for sending detection data is transmitted periodically, for example, every 30 minutes from the remotely located biological signal input apparatus to the Holter electrocardiograph, the conditions of the patient can be grasped in time series and moreover the biological signal input apparatus can always make proper data analysis easily and promptly.

In the communication system of the invention, data different from the disease conditions of the patient, such as an electrode detachment state from the patient and a radio wave cutoff state with the transmitter-receiver can be detected reliably, so that the reliability of the detection data of a biological signal can be enhanced sufficiently and the accuracy of the data analysis result can also be enhanced; the advantages for patient management are extremely large.

The disclosures of U.S. Ser. No. 09/220,751 are incorporated herein by reference.

What is claimed is:

1. A biological signal detection system, comprising:

a plurality of first electrodes for detecting a biological signal;

a plurality of second electrodes for detecting the biological signal;

a first support, supporting the first electrodes and adapted to be disposed on a living body so that a first one of the first electrode is located on a first position of the living body and a second one of the first electrodes is located on a second position of the living body;

a second support, supporting a first one of the second electrodes and adapted to be disposed on the living body so that the first one of the second electrodes is located on a third position of the living body;

a third support, supporting a second one of the second electrodes and adapted to be disposed on the living body so that the second one of the second electrodes is located on a forth position of the living body;

a forth support, supporting a third one of the second electrodes and adapted to be disposed on the living body so that the third one of the second electrodes is located on a fifth position of the living body a fifth support, supporting a forth one of the second electrodes and adapted to be disposed on the living body so that the forth one of the second electrodes is located on a sixth position of the living body;

a transmitter, adapted to be disposed on the living body, comprising an electric circuit operable to process the biological signal and to telemeter the processed signal;

a first connection section for electrically connecting the plurality of first electrodes to the transmitter; and a second connection section for electrically connecting the plurality of second electrodes to the transmitter;

a biological signal inputting apparatus;

a receiver-transmitter, adapted to be disposed on the living body, and operable to receive the processed signal telemetered from the transmitter and to telemeter the processed signal to the biological signal inputting apparatus using a wide area network; and a storage, adapted to be removably attached to the receiver-transmitter for storing the processed signal telemetered from the transmitter as biological signal data, wherein the first support, the second support, the third support, the fourth support and the fifth support are independent from each other so that relative distances there-between are variable;

when the first one of the first electrodes, the second one of the first electrodes, the first one of the second electrodes, the second one of the second electrodes, the third one of the second electrodes, and the forth one of the second electrodes are respectively located on the first position, the second position, the third position, the forth position, the fifth position and the sixth position, at least one CM5 lead is established between the first position and the third position, at least one NASA lead is established between the second position and the fourth position, and at least one CC5 lead is established between the fifth position and the sixth position simultaneously; and wherein the electric circuit processes the at least one CM5 lead, the at least one NASA lead and the at least one CC5 lead to generate a CM5, a NASA, and a CC5 lead signal respectively.

2. The system of claim 1, wherein the storage is also adapted to be removably attached to the biological signal inputting apparatus for inputting the biological signal data to the biological signal inputting apparatus.

3. The system of claim 1, wherein the receiver-transmitter is operable to receive an instruction from the biological signal inputting apparatus, and wherein the receiver-transmitter is operable to telemeter the processed signal in response to the instruction.

4. A biological signal detection system, comprising:

a plurality of first electrodes for detecting a biological signal;

a plurality of second electrodes for detecting the biological signal;

a first support, supporting the first electrodes and adapted to be disposed on a living body so that a first one of the first electrode is located on a first position of the living body and a second one of the first electrodes is located on a second position of the living body;

a second support, supporting a first one of the second electrodes and adapted to be disposed on the living body so that the first one of the second electrodes is located on a third position of the living body;

a third support, supporting a second one of the second electrodes and adapted to be disposed on the living body so that the second one of the second electrodes is located on a forth position of the living body;

a forth support, supporting a third one of the second electrodes and adapted to be disposed on the living body so that the third one of the second electrodes is located on a fifth position of the living body a fifth support, supporting a forth one of the second electrodes and adapted to be disposed on the living body so that the forth one of the second electrodes is located on a sixth position of the living body;

a transmitter, adapted to be disposed on the living body, comprising an electric circuit operable to process the biological signal and to telemeter the processed signal;

a first connection section for electrically connecting the plurality of first electrodes to the transmitter; and a second connection section for electrically connecting the plurality of second electrodes to the transmitter;

a receiver, adapted to be disposed on the living body, and operable to receive the processed signal telemetered from the transmitter; and a storage, adapted to be removably attached to the receiver for storing the processed signal telemetered from the transmitter as biological signal data, wherein the first support, the second support, the third support, the fourth support and the fifth support are independent from each other so that relative distances there-between are variable;

when the first one of the first electrodes, the second one of the first electrodes, the first one of the second electrodes, the second one of the second electrodes, the third one of the second electrodes, and the forth one of the second electrodes are respectively located on the first position, the second position, the third position, the forth position, the fifth position and the sixth position, at least one CM5 lead is established between the first position and the third position, at least one NASA lead is established between the second position and the fourth position, and at least one CC5 lead is established between the fifth position and the sixth position simultaneously, and wherein the electric circuit processes the at least one CM5 lead, the at least one NASA lead and the at least one CC5 lead to generate a CM5, a NASA, and a CC5 lead signal respectively.

5. The system of claim 4, wherein the storage is also adapted to be removably attached to a remote biological signal inputting apparatus for inputting the biological signal data to the biological signal inputting apparatus.

6. A biological signal detection system, comprising:

a plurality of first electrodes for detecting a biological signal;

a plurality of second electrodes for detecting the biological signal;

a first support, supporting the first electrodes and adapted to be disposed on a living body so that a first one of the first electrode is located on a first position of the living body and a second one of the first electrodes is located on a second position of the living body;

a second supports, supporting a first one of the second electrodes and adapted to be disposed on the living body so that the first one of the second electrodes is located on a third position of the living body;

a third support, supporting a second one of the second electrodes and adapted to be disposed on the living body so that the second one of the second electrodes is located on a forth position of the living body;

a forth support, supporting a third one of the second electrodes and adapted to be disposed on the living body so that the third one of the second electrodes is located on a fifth position of the living body a fifth support, supporting a forth one of the second electrodes and adapted to be disposed on the living body so that the forth one of the second electrodes is located on a sixth position of the living body;

a transmitter, adapted to be disposed on the living body, comprising an electric circuit operable to process the biological signal and to telemeter the processed signal;

a first connection section for electrically connecting the plurality of first electrodes to the transmitter; and a second connection section for electrically connecting the plurality of second electrodes to the transmitter; and a storage, adapted to be removably attached to the transmitter for storing the processed signal as biological signal data, wherein the first support, the second support, the third support, the fourth support and the fifth support are independent from each other so that relative distances there-between are variable;

when the first one of the first electrodes, the second one of the first electrodes, the first one of the second electrodes, the second one of the second electrodes, the third one of the second electrodes, and the forth one of the second electrodes are respectively located on the first position, the second position, the third position, the forth position, the fifth position and the sixth position, at least one CM5 lead is established between the first position and the third position, at least one NASA lead is established between the second position and the fourth position, and at least one CC5 lead is established between the fifth position and the sixth position simultaneously, and wherein the electric circuit processes the at least one CM5 lead, the at least one NASA lead and the at least one CC5 lead to generate a CM5, a NASA, and a CC5 lead signal respectively.

7. The system of claim 6, wherein the storage is also adapted to be removably attached to a remote biological signal inputting apparatus for inputting the biological signal data to the biological signal inputting apparatus.

* * * * *